(12) United States Patent
Friede et al.

(10) Patent No.: US 6,544,518 B1
(45) Date of Patent: Apr. 8, 2003

(54) VACCINES

(75) Inventors: Martin Friede, Farnham (GB); Nathalie Garcon, Wavre (BE); Catherine Marie Ghislaine Gerard, Rhode Saint Genese (BE); Philippe Hermand, Court-Saint-Etienne (BE)

(73) Assignee: SmithKline Beecham Biologicals s.a., Rixensart (BE)

( * ) Notice: Subject to any disclaimer, the term of this patent is extended or adjusted under 35 U.S.C. 154(b) by 0 days.

(21) Appl. No.: 09/690,921

(22) Filed: Oct. 18, 2000

Related U.S. Application Data

(63) Continuation-in-part of application No. PCT/EP00/02920, filed on Apr. 4, 2000, and a continuation-in-part of application No. 09/301,829, filed on Apr. 29, 1999.

(30) Foreign Application Priority Data

Apr. 19, 1999 (GB) ............................................. 9908885

(51) Int. Cl.⁷ ......................... A61K 39/00; A61K 39/39
(52) U.S. Cl. ................................ 424/184.1; 424/184.1; 424/278.1; 424/283.1; 424/208.1; 424/228.1; 424/229.1; 424/231.1; 424/249.1; 514/25
(58) Field of Search ........................... 424/184.1, 278.1, 424/283.1, 208.1, 231.1, 249.1, 263.1, 258.1, 229.1, 226.1, 227.1, 228.1; 514/25

(56) References Cited

U.S. PATENT DOCUMENTS

| | | | |
|---|---|---|---|
| 5,057,540 A | 10/1991 | Kensil et al. | |
| 6,231,859 B1 | * 5/2001 | Kensil | ................... 424/184.1 |
| 6,406,705 B1 | 6/2002 | Davis et al. | ............. 424/278.1 |

FOREIGN PATENT DOCUMENTS

| EP | 0 109 942 B1 | 3/1991 |
|---|---|---|
| EP | 0 468 520 | 7/1991 |
| EP | 0 362 279 | 1/1995 |
| EP | 0 671 948 | 8/1997 |
| EP | 0 689 454 | 9/1997 |
| EP | 0 855 184 | 7/1998 |
| GB | 2 122 204 A | 1/1984 |
| WO | WO95/17210 | 6/1995 |
| WO | WO96/02555 | 2/1996 |
| WO | WO96/11711 | 4/1996 |
| WO | WO96/33739 | 10/1996 |
| WO | WO98/15287 | 4/1998 |
| WO | WO98/16247 | 4/1998 |
| WO | WO 98/18810 | 5/1998 |
| WO | WO98/20734 | 5/1998 |
| WO | WO98/28037 | 7/1998 |
| WO | WO 98/37919 | 9/1998 |
| WO | WO 98/40100 | 9/1998 |
| WO | WO 98/55495 | 12/1998 |
| WO | WO 98/55609 | 12/1998 |
| WO | WO98/56414 | 12/1998 |
| WO | WO98/56415 | 12/1998 |
| WO | WO99/10008 | 3/1999 |
| WO | WO 99/12565 | 3/1999 |
| WO | WO 99/33488 | 7/1999 |
| WO | WO 99/61056 | 12/1999 |
| WO | WO 99/62923 | 12/1999 |
| WO | WO 00/09159 | 2/2000 |

OTHER PUBLICATIONS

Dennis M. Klinman, "Therapeutic Applications of CpG–Containing Oligodeoxynucleotides", *Antisense & Nucleic Acid Drug Development*, 8: 181–184 (1998).

Liu, et al., "Immunostimulatory CpG Oligodeoxynucleotides Enhance the Immune Response to Vaccine Strategies Involving Granulocyte–Macrophage Colony–Stimulating Factor", *Blood*, 92(10): 3730–3736 (1998).

Kreig, et al., The Role of CpG Dinucleotides in DNA Vaccines *Trends in Microbiology*, 6(1): 23–27 (1998).

So, et al., "Effect of a Novel Saponin Adjuvant Derived from *Quillaja saponaria* on the Immune Response to Recombinant Hepatitis B Surface Antigen", *Mol. Cells*, 7(2): 178–186 (1997).

Lipford, et al., "CpG–Containing Synthetic Oligonucleotides Promote B and Cytotoxic T Cell Responses to Protein Antigen: A New Class of Vaccine Adjuvants", *Eur. J. Immunology*, 27: 2340–2344 (1997).

Moldoveanu, et al., "CpG DNA, A Novel Immune Enhancer for Systemic and Mucosal Immunization with Influenza Virus", *Vaccine*, 16: 1216–1224 (1998).

Klinman, et al., "CpG Motifs as Immune Agjuvants", *Vaccine*, 17: 19–25, (1999).

Mowat et al., "Immune–stimulating complexes containing !uil A and protein antigen prime class etc.", *Immunology*, 72, pp. 317–322 (1991).

Kensil et al., "Synergistic Action of QS–21 and CpG Adjuvants", *X5 DNA Vaccines*, Abstract No. 218, (1999).

O. Gisvold, "Digitonin and Phytosterol From the See of Digitalis Purpurea", *Phytochemical Notes*, 23(7), pp. 664–665 (1933).

Yoshikawa et al., "Bioactive Saponins and Glycosides, III. Horse Chestnur (1): etc.", *Chem. Phar. Bull.*, 44(8), pp. 1454–1463 (1996).

(List continued on next page.)

Primary Examiner—Laurie Scheiner
(74) Attorney, Agent, or Firm—Jeffery A. Sutton; Stephen Venetianer; Charles M. Kinzig

(57) ABSTRACT

The present invention relates to adjuvant compositions which are suitable to be used in vaccines. In particular, the adjuvant compositions of the present invention comprises a saponin and an immunostimulatory oligonucleotide, optionally with a carrier. Also provided by the present invention are vaccines comprising the adjuvants of the present invention and an antigen. Further provided are methods of manufacture of the adjuvants and vaccines of the present invention and their use as medicaments. Methods of treating an individual susceptible to or suffering from a disease by the administration of the vaccines of the present invention are also provided.

15 Claims, 12 Drawing Sheets

OTHER PUBLICATIONS

Figure 1:
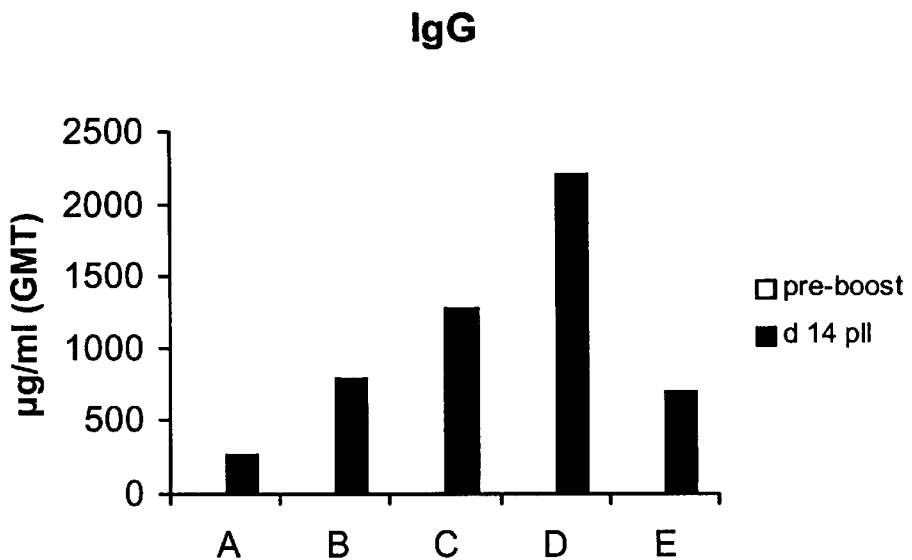
Figure 2:
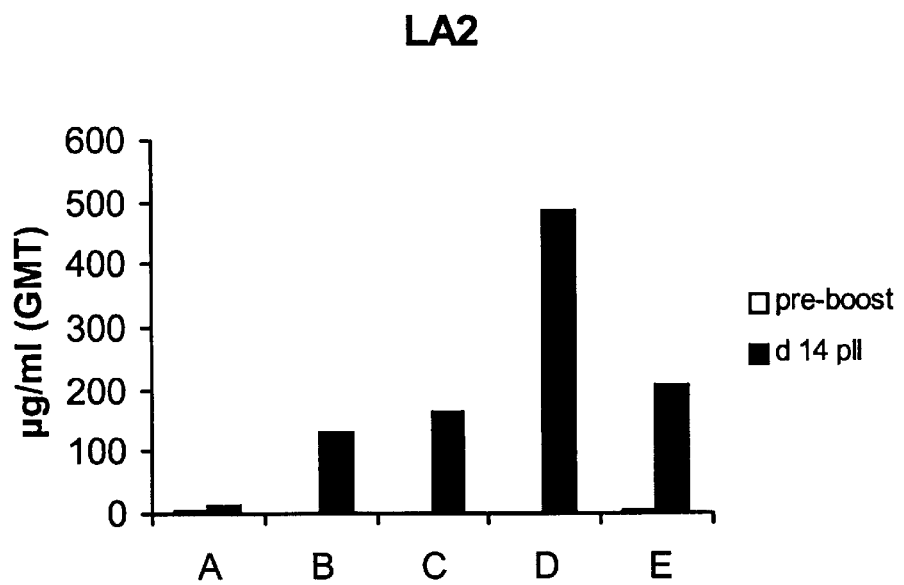

Estrada et al., "Adjuvanta ction of Chenopodium quinoa saponins on the induction etc.", *Com. Immun. Microbiol. & Infect Dis.*, 21, pp. 225–236 (1998).

Kensil, "Saponins as Vaccines Adjuvants", *Critical Reviews in Therapeutic Drug Carrier Systems*, 13(1&2), pp. 1–55 (1996).

Lacaille–Dubois et al., "A review of the biological and pharmacological activities of saponins", *Phytomedicine*, 2(4), pp. 363–386 (1996).

Gizurarson et al., "Pharmaceutical Excipients and Absorpotion Promoters as Immunostimulatns etc.", *Vacgine Research*, 3(1), pp. 23–29 (1994).

Bomford et al., "Adjuvanticity and ISCOM formation by structually diverse saponins", *Vaccine*, 10(9), pp. 572–577 (1992).

Krieg et al., "CpG motifs in bacterial DNA trigger direct B–cell activation", *Nature*, 374, pp. 546–549 (1995).

Kensil et al., "Separation and Characterization of Saponins with adjuvant Activity etc.", *Journal of Immunology*, 146(2), pp. 431–437 (1991).

Chavali et al., "Adjuvant Effects of Orally Administered Saponins on Humoral etc." *Immunobiol.*, 174, pp. 347–359 (1987).

Sasaki et al., "Induction of Systemic and Mucosal Immune Responses to Human etc.", *Journal of Virology*, 72(6), pp. 4931–4939 (1998).

Majarak et al., "Immune responses of mice to inactivated rabies vaccine etc.", *Can. J. Microbiol.*, 32, pp. 414–420 (1986).

Mowat et al., "ISCOMS–a novel strategy for mucosal immunization?", Immunology Today, 12(11), pp. 383–385 (1991).

Brazolot–Millan et al., "CpG DNA can induce strong Th1 humoral and cell–mediated immune etc.", *Proc. Natl. Acad. Sci. USA*, 95, pp. 15553–15558 (1988).

McCluskie et al., "Cutting Edge:CpG DNA is a potent enhancer of systemic and mucosal etc.", *J. Immunol.*, 161(9), pp. 4463–4466 (1998).

Davis et al., "CpG DNA ia patent enhancer of specific immunity in mice etc.", *J. Immunol.*, 160(2), pp. 870–876 (1998).

* cited by examiner

Serum IgG to lipo-OspA in mice

LA2 titres in mice

Serum IgG titres to flu strains

Serum HAI titres

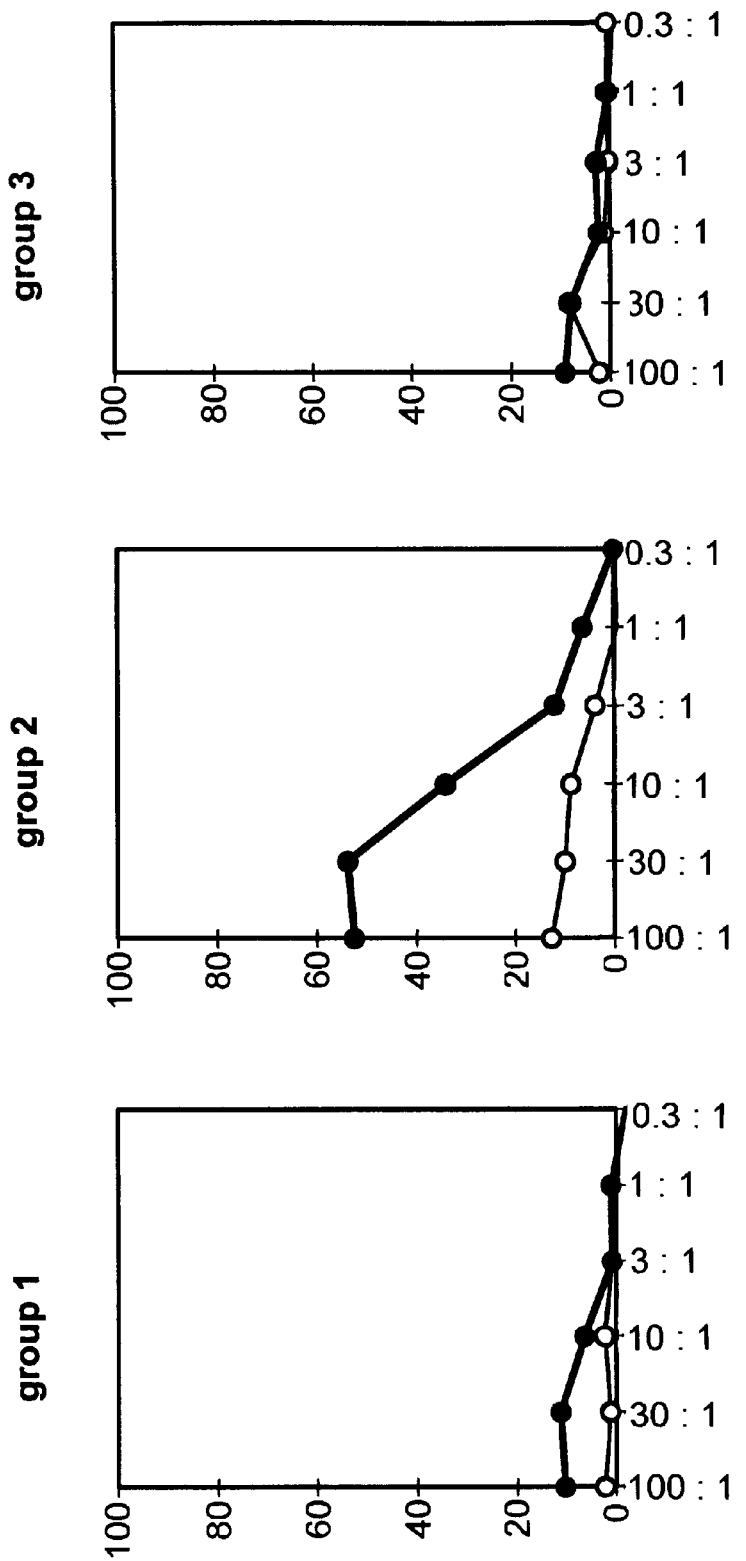

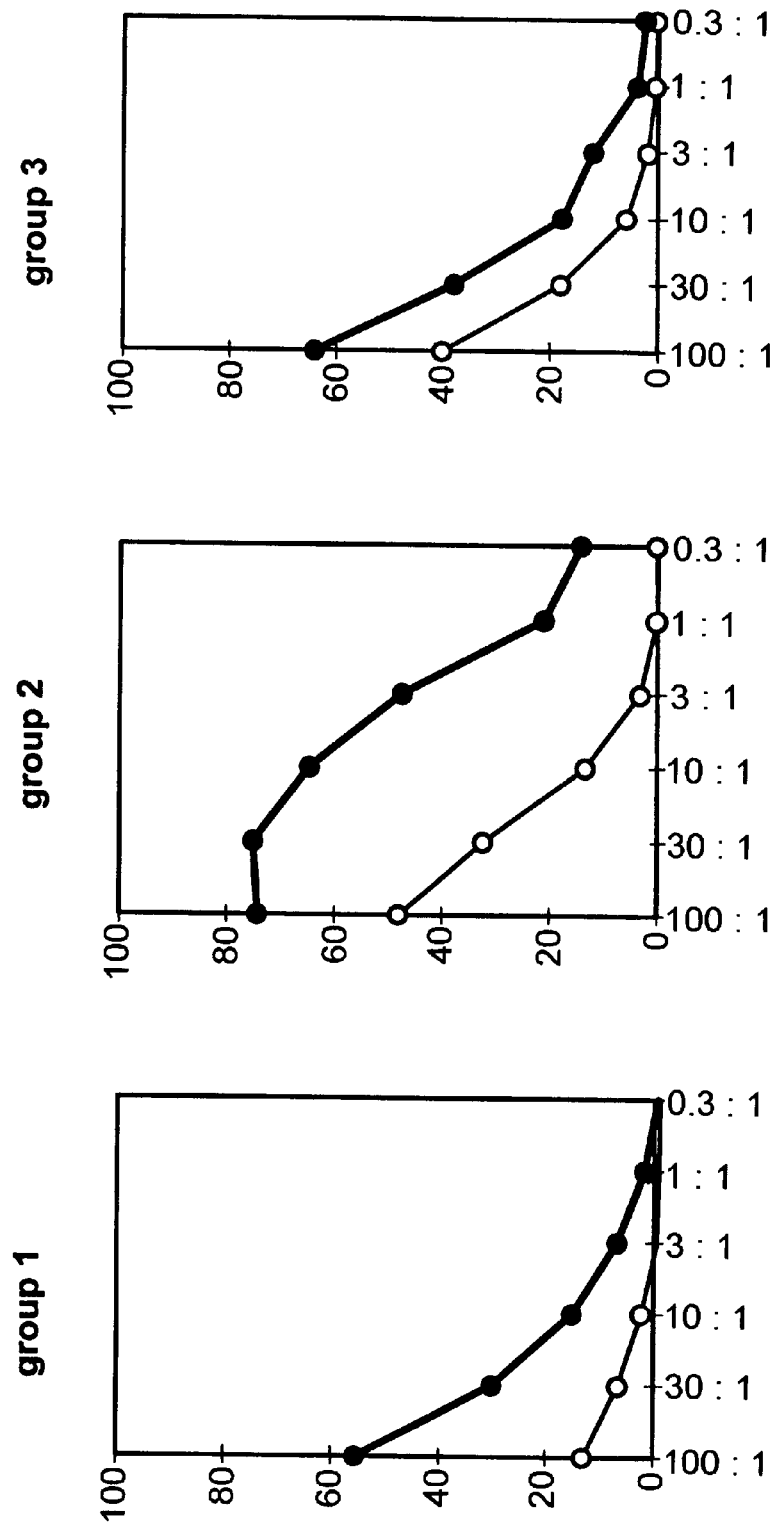

HbsAg-specific and gp120-specific antibody titres

*HBsAg-specific antibody titers*

| formulations | Igtot UE/ml |
|---|---|
| group 1 | 11536 |
| group 2 | 30629 |
| group 3 | 50540 | gp120-specific antibody titers

| formulations | Igtot µg/ml |
|---|---|
| group 1 | 24 |
| group 2 | 62 |
| group 3 | 92 |

VACCINES

This application is a continuation-in-part of PCT/EP00/02920 filed Apr. 4, 2000 and a continuation-in-part of Ser. No. 09/301,829 filed Apr. 29, 1999.

The present invention relates to novel adjuvant compositions for use in vaccines. In particular, the adjuvant compositions of the present invention comprise a combination of a saponin, and an immunostimulatory oligonucleotide, optionally with a lipopolysacharide. Also provided by the present invention are vaccines comprising the adjuvant compositions of the present invention and at least one antigen. Further provided are methods of manufacture of the adjuvant compositions and vaccines of the present invention and their use as medicaments. Additionally, the present invention provides methods of treating an individual susceptible to or suffering from a disease by the parenteral or mucosal administration of the vaccines of the present invention.

Immunostimulatory oligonucleotides containing ummethylated CpG dinucleotides ("CpG") and are known in the art as being adjuvants when administered by both systemic and mucosal routes (WO 96/02555, EP 468520, Davis et al., J.Immunol, 1998. 160(2):870–876; McCluskie and Davis, J.Immunol., 1998, 161(9):4463–6). CpG is an abbreviation for cytosine-guanosine dinucleotide motifs present in DNA. Historically, it was observed that the DNA fraction of BCG could exert an anti-tumour effect. In further studies, synthetic oligonucleotides derived from BCG gene sequences were shown to be capable of inducing immunostimulatory effects (both in vitro and in vivo). The authors of these studies concluded that certain palindromic sequences, including a central CG motif, carried this activity. The central role of the CG motif in immunostimulation was later elucidated in a publication by Krieg, Nature 374, p546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in the present invention.

In certain combinations of the six nucleotides a palindromic sequence is present. Several of these motifs, either as repeats of one motif or a combination of different motifs, can be present in the same oligonucleotide. The presence of one or more of these immunostimulatory sequence containing oligonucleotides can activate various s immune subsets, including natural killer cells (which produce interferon y and have cytolytic activity) and macrophages (Wooldrige et al Vol 89 (no. 8), 1977). Although other unmethylated CpG containing sequences not having this consensus sequence have now been shown to be immunomodulatory.

CpG when formulated into vaccines, is generally administered in free solution together with free antigen (WO 96/02555; McCluskie and Davis, supra) or covalently conjugated to an antigen (PCT Publication No. WO 98/16247), or formulated with a carrier such as aluminium hydroxide ((Hepatitis surface antigen) Davis et al. supra Brazolot-Millan et al., Proc.Natl.Acad.Sci., USA, 1998, 95(26), 15553–8).

Saponins are taught in: Lacaille-Dubois, M and Wagner H. (1996. A review of the biological and pharmacological activities of saponins. Phytomedicine vol 2 pp 363–386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja Saponaria Molina), and fractions thereof, are described in U.S. Pat. No. 5,057,540 and "Saponins as vaccine adjuvants", Kensil, C. R., Crit Rev Ther Drug Carrier Syst, 1996, 12 (1–2):1–55, and EP 0 362 279 B1.

Particulate structures, termed Immune Stimulating Complexes (ISCOMS), comprising fractions of Quil A are haemolytic and have been used in the manufacture of vaccines (Morein, B., EP 0 109 942 B1). These structures have been reported to have adjuvant activity (EP 0 109 942 B1; WO 96/11711).

The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology vol 146, 431–437). Combinations of QS21 and polysorbate or cyclodextrin arc also known (WO 99/10008). Particulate adjuvant systems comprising fractions of QuilA, such as QS21 and QS7 are described in WO 96/33739 and WO 96/11711.

Other saponins which have been used in systemic vaccination studies include those derived from other plant species such as Gypsophila and Saponaria (Bomford et al., Vaccine, 10(9):572–577, 1992).

Saponins are also known to have been used in mucosally applied vaccine studies, which have met with variable success in the induction of immune responses. Quil-A saponin has previously been shown to have no effect on the induction of an immune response when antigen is administered intranasally (Gizurarson et al. 1994. Vaccine Research 3, 23–29). Whilst, other authors have used this adjuvant with success (Maharaj et al., Can.J.Microbiol, 1986, 32(5): 414–20: Chavali and Campbell, Immunobiology, 174(3) 347–59). ISCOMs comprising Quil A saponin have been used in intragastric and intranasal vaccine formulations and exhibited adjuvant activity (McI Mowat et al., 1991, Immunology, 72, 317–322; McI Mowat and Donachie, Immunology Today, 12, 383–385).

QS21, the non-toxic fraction of Quil A, has also been described as an oral or intranasal adjuvant (Sumino et al., J.Virol., 1998, 72(6):4931–9: WO 98/56415).

The use of other saponins in intranasal vaccination studies has been described. For example, Chenopodium quinoa saponins has been used in both intranasal and intragastric vaccines (Estrada et al., Comp. Immunol. Microbiol. Infect. Dis., 1998, 21(3):225–36).

The present invention relates to the surprising finding that immunostimulatory oligonucleotides (CpG) and saponin combinations are extremely potent adjuvants. Accordingly, there is provided an adjuvant composition comprising a combination of saponin and an immunostimulatory oligonucleotide. Preferably, the adjuvants of the present invention may further comprise a carrier. In a preferred form of the present invention the saponin and oligonucleotides in the adjuvant and vaccine compositions act synergistically in the induction of antigen specific antibody and are potent in the induction of immune responses conventionally associated with the Th1-type immune system. Accordingly, the adjuvant combinations are not only suitable for immunoprophylaxis of diseases, but also surprisingly for immunotherapy of diseases such as persistant viral, bacterial or parasitic infections, and also chronic disorders such as cancer.

The preferred oligonucleotides for use in adjuvants or vaccines of the present invention preferably contain two or more dinucleotide CpG motifs separated by at least three, more preferably at least six or more nucleotides. The oligonucleotides of the present invention are typically deoxynucleotides. In a preferred embodiment the internucleotide in the oligonucleotide is phosphorodithioate, or more preferably a phosphorothioate bond, although phosphodiester and other internucleotide bonds are within the scope of the invention including oligonucleotides with mixed internucleotide linkages. Methods for producing phosphorothioate oligonucleotides or phosphorodithioate are described in U.S. Pat. Nos. 5,666,153, 5,278,302 and WO95/26204.

Examples of preferred oligonucleotides have the following sequences. The sequences preferably contain phosphorothioate modified internucleotide linkages.

OLIGO 1(SEQ ID NO:1): TCC ATG ACG TTC CTG ACG TT (CpG 1826)
OLIGO 2 (SEQ ID NO:2): TCT CCC AGC GTG CGC CAT (CpG 1758)
OLIGO 3(SEQ ID NO:3): ACC GAT GAC GTC GCC GGT GAC GGC ACC ACG
OLIGO 4 (SEQ ID NO:4): TCG TCG TTT TGT CGT TTT GTC GTT (CpG 2006)
OLIGO 5 (SEQ ID NO:5): TCC ATG ACG TTC CTG ATG CT (CpG 1668)

Alternative CpG oligonucleotides may comprise the preferred sequences above in that they have inconsequential deletions or additions thereto. The CpG oligonucleotides utilised in the present invention may be synthesized by any method known in the art (eg EP 468520). Conveniently, such oligonucleotides may be synthesized utilising an automated synthesizer The oligonucleotides utilised in the present invention are typically deoxynucleotides. In a preferred embodiment the internucleotide bond in the oligonucleotide is phosphorodithioate, or more preferably phosphorothioate bond, although phosphodiesters are within the scope of the present invention. Oligonucleotide comprising different internucleotide linkages are contemplated, e.g. mixed phosphorothioate phophodiesters. Other internucleotide bonds which stabilise the oligonucleotide may be used.

The saponins which may be used in the adjuvant combinations of the present invention include those derived from the bark of *Quillaja Saponaria Molina*, termed Quil A, and fractions thereof, described in U.S. Pat. No. 5,057,540 and "Saponins as vaccine adjuvants", Kensil, C. R., *Crit Rev Ther Drug Carrier Syst*, 1996, 12 (1–2):1–55; and EP 0 362 279 B 1. Particularly preferred fractions of Quil A are QS21. QS7, and QS17.

–Escin is another preferred haemolytic saponins for use in the adjuvant compositions of the present invention. Escin is described in the Merck index (12$^{th}$ ed: entry 3737) as a mixture of saponin occurring in the seed of the horse chestnut tree, Lat: *Aesculus hippocastanum*. Its isolation is described by chromatography and purification (Fiedler, *Arzneimittel-Forsch.* 4, 213 (1953)), and by ion-exchange resins (Erbring et al., U.S. Pat. No. 3,238,190). Fractions of escin, and, have been purified and shown to be biologically active (Yoshikawa M, et al. (*Chem Pharm Bull* (Tokyo) 1996 August;44(8): 1454–1464)). –escin is also known as aescin.

Another preferred haemolytic saponin for use in the present invention is Digitonin. Digitonin is described in the Merck index (12$^{th}$ Edition, entry 3204) as a saponin, being derived from the seeds of *Digitalis purpurea* and purified according to the procedure described Gisvold et al., *J.Am. Pharm.Assoc.*, 1934, 23, 664; and Rubenstroth-Bauer, *Physiol. Chem.*, 1955, 301, 621. Its use is described as being a clinical reagent for cholesterol determination.

The adjuvant combinations of the present invention may further comprise a carrier, such that the saponin or CpG, or both, may be associated with a particulate carrier entity to enhance the adjuvanticity of the combination. Particularly preferred systemic vaccines, for example, comprise a carrier molecule.

The CpG used in the adjuvant combinations of the present invention may be in free solution or may be complexed to particulate carriers such as mineral salts (for example, but not restricted to, aluminium or calcium salts), liposomes, ISCOMs, emulsions (oil in water, water in oil, water in oil in water), polymers (such as, but not restricted to polylactic, polyglycolic, polyphosphazine, polyaminoacid, alginate, chitosan) or microparticles. Preferably said carriers are cationic. The vaccines of the present invention further comprise an antigen which may be associated with the CpG-carrier complex, or may not be associated with the CpG-carrier complex. In this case, the antigen may be free suspension or associated with a separate carrier.

The saponins forming part of the present invention may be separate in the form of micelles, or may be in the form of large ordered structures such as ISCOMs (EP 0 109 942 B1) or liposomes (WO 96/33739) when formulated with cholesterol and lipid, or in the form of an oil in water emulsion (WO 95/17210). The saponins may preferably be associated with a metallic salt, such as aluminium hydroxide or aluminium phosphate (WO 98/15287). Alternatively the saponin may be associated with a particulate carrier such as chitosan. The saponin may also be in a dry state such as a powder. The final formulations in the form as they are administered to the mucosal surface of the vaccinee are preferably haemolytic in nature. The saponin may or may not be associated physically with the antigen either through direct linkage or by co-interaction with the same particulate carrier molecule (GB9822712.7; WO 98/16247). The CpG and saponin in the adjuvants or vaccines of the present invention may themselves be separate or associated. For example, the CpG and saponin may be in free suspension or may be associated via a carrier, more preferably a particulate carrier such as aluminium hydroxide or by a cationic liposome or ISCOM.

A preferred adjuvant combination according to the present invention is composed of one or more CpG oligonucleotides containing at least 3, preferably at least 6 nucleotides between two adjacent CG motifs, together with QS21 and a particulate carrier selected from the group comprising an oil-in-water emulsion or DQ. Most preferably, the adjuvant combination comprises CpG 2006 (SEQ ID NO: 4), or CpG 1758 (SEQ ID NO: 2) or CpG 1826 (SEQ ID NO: 1) mixed with QS21, and a particulate carrier selected from the group comprising an oil-in-water emulsion or DQ. Accordingly, particularly preferred vaccines, for example, comprise such adjuvant combinations and an antigen. The preferred vaccine of the present invention is used to generate systemic immune responses after administration to an individual through the systemic route.

The adjuvant combinations of the present invention may be used as both systemic or mucosal adjuvant. In a particular form of the invention there is provided a systemic vaccine to be administered through the systemic or parenteral route such as intramuscular, intradermal, transdermal, subcutaneous, intraperitoneal or intravenous administration. A preferred route of administration is via the transdermal route, for example by skin patches.

The systemic vaccine preparations of the present invention may be used to protect or treat a mammal susceptible to, or suffering from disease, by means of administering said vaccine by intramuscular, intraperitoneal, intradermal, transdermal, intravenous, or subcutaneous administration. Methods of systemic administration of the vaccine preparations may include conventional syringes and needles, or devices designed for ballistic delivery of solid vaccines (WO 99/27961), or needleless pressure liquid jet device (U.S. Pat. Nos. 4,596,556; 5,993,412), or transdermal patches (WO 97/48440; WO 98/28037). The present invention may also be used to enhance the immunogenicity of antigens applied to the skin (transdermal or transcutaneous delivery WO 98/20734 WO 98/28037). The present invention therefore provides a delivery device for systemic administration, pre-filled with the vaccine or adjuvant compositions of the present invention. Accordingly there is provided a method for inducing an immune response in an individual, comprising the administration of a vaccine comprising an antigen and immunostimulatory oligonucleotide, a saponin, and a carrier, to the individual, wherein the vaccine is administered via the parenteral or systemic route. Preferred methods of inducing an immune response comprises the administration of a vaccine comprising an oligonucleotide of SEQ ID NO: 1, 2, 3, 4 or 5, with a saponin derived from QuilA, such as QS21, and a carrier, such as an oil in water emulsion, a cholesterol containing liposome or alum.

Alternatively the vaccine preparations of the present invention may be used to protect or treat a mammal susceptible to, or suffering from disease, by means of administering said vaccine via a mucosal route, such as the oral/alimentary or nasal route. Alternative mucosal routes are intravaginal and intra-rectal. The preferred mucosal route of administration is via the nasal route, termed intranasal vaccination. Methods of intranasal vaccination are well known in the art, including the administration of a droplet, spray, or dry powdered form of the vaccine into the nasopharynx of the individual to be immunised. Nebulised or aerosolised vaccine formulations also form part of this invention. Enteric formulations such as gastro resistant capsules and granules for oral administration, suppositories for rectal or vaginal administration also form part of this invention.

The adjuvant combinations of the present invention, represent a class of mucosal adjuvants suitable for application in humans to replace systemic vaccination by mucosal vaccination. In a preferred form of the present invention pure saponins such as Quil A, or derivatives thereof, including QS21; Escin; Digitonin; or Gypsophila or *Chenopodium quinoa* saponins in combination with immunostimulatory oligonucleotides may be used as adjuvants for the mucosal administration of antigens to achieve a systemic immune response.

The adjuvant combinations of the present invention are used in the formulation of vaccines, which vaccines may be administered via the systemic or mucosal route. Preferably, when the vaccines are used for mucosal administration the adjuvant combination comprises a haemolytic saponin.

For mucosal administration preferably the composition of the invention comprise a haemolytic saponin. Haemolytic saponin, or saponin preparation, within the meaning of this invention is to be determined with reference to the following assay.

1. Fresh blood from guinea pigs is washed with phosphate buffered saline (PBS) 3 times in a desk-top centrifuge. After resuspension to the original volume the blood is further diluted 10 fold in PBS.
2. 50 μl of this blood suspension is added to 800 μl of PBS containing two-fold dilutions of surfactant or saponin.
3. After 8 hours the haemolysis is assessed visually or by measuring the optical density of the supernatant. The presence of a red supernatant, which absorbs light at 570 nm indicates the presence of haemolysis.
4. The results are expressed as the concentration of the first saponin dilution at which hemolysis no longer occurs.

For the purposes of this invention the saponin adjuvant preparation is haemolytic if it lyses the erythrocytes at a concentration of less than 0.1%. As means of reference, substantially pure samples of QuilA. QS21, QS7, Digitonin, and -escin are all haemolytic saponins as defined in this assay. Within the inherent experimental variability of such a biological assay, the saponins of the present invention preferably have a haemolytic activity, of approximately between 0.5–0.00001%, more preferably between 0.05–0.00001%, even more preferably between 0.005–0.00001%, and most preferably between 0.001–0.0004%. Ideally, said saponins should have a haemolytic activity similar (i. e. within a ten-fold difference) to that of QS21.

The vaccines of the present invention may also be administered via the oral route. In such cases the pharmaceutically acceptable excipient may also include alkaline buffers, or enteric capsules or microgranules. The vaccines of the present invention may also be administered by the vaginal route. In such cases, the pharmaceutically acceptable excipients may also include emulsifiers, polymers such as CARBOPOL®, and other known stabilisers of vaginal creams and suppositories. The vaccines of the present invention may also be administered by the rectal route. In such cases the excipients may also include waxes and polymers known in the art for forming rectal suppositories.

Preparations of more than one saponin in the adjuvant combinations of the present invention are also form part of the present invention. For example combinations of at least two of the following group comprising QS21, QS7, Quil A, β-escin, or digitonin. Additionally, the compositions of the present invention may comprise combinations of more than one immunostimulatory oligonucleotide.

In a similar embodiment of the present invention the CpG/saponin combinations for both systemic and mucosal administration may be further combined with other adjuvants including lipopolysaccharide or a derivative thereof.

The adjuvant combinations of the present invention include in an embodiment, at least enterobacterial lipopolysaccharide derived adjuvant.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of bacterial endotoxins, Plenum Publ. Corp., NY, p407–419) and has the following structure:

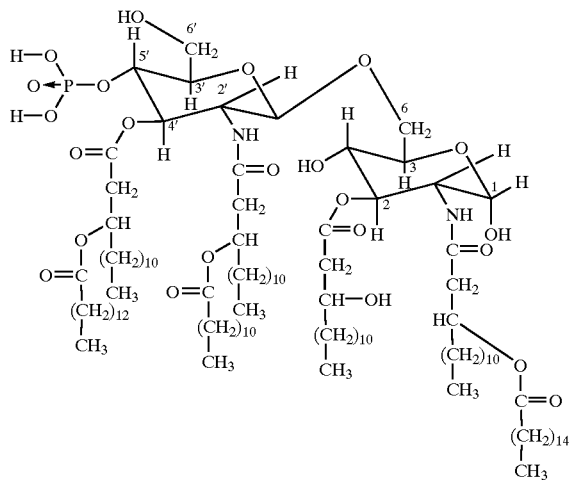

A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof. A preferred form of 3D-MPL is in the form of an emulsion having a small particle size less than 0.2 μm in diameter, and its method of manufacture is disclosed in WO 94/21292. Aqueous formulations comprising monophosphoryl lipid A and a surfactant have been described in WO9843670A2.

The bacterial lipopolysaccharide derived adjuvants to be formulated in the adjuvant combinations of the present invention may be purified and processed from bacterial sources, or alternatively they may be synthetic. For example, purified monophosphoryl lipid A is described in Ribi et at 1986 (supra), and 3-O-Deacylated monophosphoryl or diphosphoryl lipid A derived from *Salmonella sp.* is described in GB 2220211 and U.S. Pat. No. 4,912,094. Other purified and synthetic lipopolysaccharides have been described (WO 98/01139; U.S. Pat. No. 6,005,099 and EP 0 729 473 B1. Hilgers et al., 1986, *Int.Arch.Allergy.Immunol.*, 79(4):392–6; Hilgers et at., 1987, Immunology, 60(1); 141–6; and EP 0 549 074 B1). Particularly preferred bacterial lipopolysaccharide adjuvants are 3D-MPL and the β(1–6) glucosamine disaccharides described in U.S. Pat. No. 6,005,099 and EP 0 729 473 B1.

Accordingly, the LPS derivatives that may be used in the present invention are those immunostimulants that are similar in structure to that of LPS or MPL or 3D-MPL. In another aspect of the present invention the LPS derivatives may be an acylated monosaccharide, which is a sub-portion to the above structure of MPL.

A preferred disaccharide adjuvant is a purified or synthetic lipid A of the following formula:

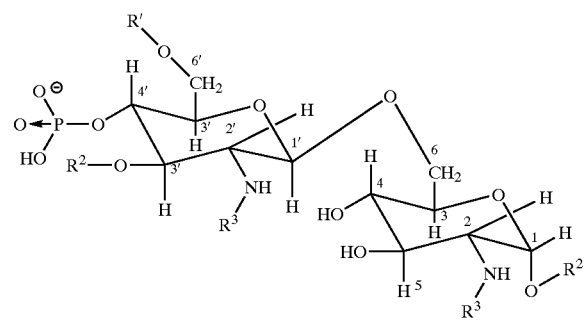

wherein R2 may be H or PO3H2. R3 may be an acyl chain or β-hydroxymyristoyl or a 3-acyloxyacyl residue having the formula:

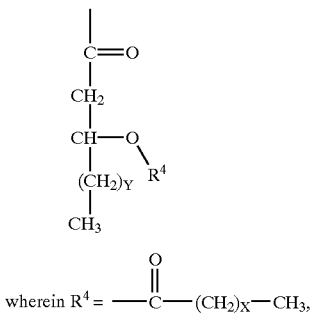

wherein $R^4 = -\overset{O}{\underset{\|}{C}}-(CH_2)_X-CH_3$, and wherein X and Y have a value of from 0 up to about 20.

Combinations of 3D-MPL and saponin adjuvants derived from the bark of Quillaja Saponaria molina have been described in EP 0 761 231B. WO 95/17210 discloses an adjuvant emulsion system based on squalene, α-tocopherol, and polyoxyethylene sorbitan monooleate (TWEEN80), formulated with the immunostimulant QS21, optionally with 3D-MPL.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol™ to increase viscosity, or may be formulated in a dry powder form with a powder excipient such as lactose.

The adjuvant combinations of the present invention can comprise an oil based emulsion. Oil emulsion adjuvants have been known for many years, including work on Freunds complete and incomplete mineral oil emulsion adjuvants. Since that time much work has been performed to design stable and well tolerated alternatives to these potent, but reactogenic, adjuvant formulations.

Many single or multiphase emulsion systems have been described. Oil in water emulsion adjuvants per se have been suggested to be useful as adjuvant composition (EP 0 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5.424,067; EP 0 480 981 B).

The oil emulsion adjuvants for use in the present invention may be natural or synthetic, and may be mineral or organic. Examples of mineral and organic oils will be readily apparent to the man skilled in the art.

In order for any oil in water composition to be suitable for human administration. the oil phase of the emulsion system preferably comprises a metabolisable oil. The meaning of the term metabolisable oil is well known in the art. Metabolisable can be defined as "being capable of being transformed by metabolism" (Dorland's illustrated Medical Dictionary, W. B. Sanders Company, 25th edition (1974)). The oil may he any vegetable oil, fish oil, animal oil or synthetic oil, which is not toxic to the recipient and is capable of being transformed by metabolism. Nuts (such as peanut oil), seeds, and grains are common sources of vegetable oils. Synthetic oils are also part of this invention and can include commercially available oils such as NEOBEE® and others. Squalene (2,6,10,15,19,23-Hexamethyl-2,6,10, 14,18,22-tetracosahexaene) is an unsaturated oil which is found in large quantities in shark-liver oil, and in lower quantities in olive oil, wheat germ nil, rice bran oil, and yeast, and is a particularly preferred oil for use in this invention. Squalene is a metabolisable oil virtue of the fact that it is an intermediate in the biosynthesis of cholesterol (Merck index, 10th Edition, entry no.8619).

Particularly preferred oil emulsions are oil in water emulsions, and in particular squalene in water emulsions.

In addition, the most preferred oil emulsion adjuvants of the present invention comprise an antioxidant, which is preferably the oil α-tocopherol (vitamin E, EP 0 382 271 B1).

WO 95/17210 and WO 99/11241 disclose emulsion adjuvants based on squalene, α-tocopherol, and TWEEN 80, optionally formulated with the immunostimulants QS21 and/or 3D-MPL. WO 99/12565 discloses an improvement to these squalene emulsions with the addition of a sterol into the oil phase. Additionally, a triglyceride, such as tricaprylin ($C_{27}H_{50}O_6$), may be added to the oil phase in order to stabilise the emulsion (WO 98/56414).

The size of the oil droplets found within the stable oil in water emulsion are preferably less than 1 micron, may be in the range of substantially 30–600 nm, preferably substantially around 30–500 nm in diameter, and most preferably substantially 150–500 nm in diameter, and in particular about 150 nm in diameter as measured by photon correlation spectroscopy. In this regard, 80% of the oil droplets by number should be within the preferred ranges, more preferably more than 90% and most preferably more than 95% of the oil droplets by number are within the defined size ranges The amounts of the components present in the oil emulsions of the present invention are conventionally in the range of from 2 to 10% oil, such as squalene; and when present, from 2 to 10% alpha tocopherol; and from 0.3 to 3% surfactant, such as polyoxyethylene sorbitan monooleate. Preferably the ratio of oil: alpha tocopherol is equal or less than 1 as this provides a more stable emulsion. Span 85 may also be present at a level of about 1%. In some cases it may be advantageous that the vaccines of the present invention will further contain a stabiliser.

The method of producing oil in water emulsions is well known to the man skilled in the art. Commonly, the method comprises the mixing the oil phase with a surfactant such as a PBS/TWEEN80™ solution, followed by homogenisation using a homogenizer, it would be clear to a man skilled in the art that a method comprising passing the mixture twice through a syringe needle would be suitable for homogenising small volumes of liquid. Equally, the emulsification process in microfluidiser (M110S microfluidics machine, maximum of 50 passes, for a period of 2 minutes at maximum pressure imput of 6 bar (output pressure of about 850 bar)) could be adapted by the man skilled in the art to produce smaller or larger volumes of emulsion. This adaptation could be achieved by routine experimentation comprising the measurement of the resultant emulsion until a preparation was achieved with oil droplets of the required diameter.

Preferably the vaccine formulations of the present invention contain an antigen or antigenic composition capable of eliciting an immune response against a human pathogen, which antigen or antigenic composition is derived from HIV-1, (such as tat, nef, gp120 or gp160), human herpes viruses, such as gD or derivatives thereof or Immediate Early protein such as ICP27 from HSV1 or HSV2, cytomegalovirus ((esp Human)(such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, . . . ), flaviviruses (e.g. Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes (as described by R. Gluck, Vaccine, 1992, 10, 915–920) or purified or recombinant proteins thereof, such as HA, NP, NA, or M proteins, or combinations thereof). or derived from bacterial pathogens such as Neisseria spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans: H. ducreyi;* Moraxella spp, including *M catarrhalis,* also known as *Branhamella catarrhalis* (for example high and low molecular weight adhesins and invasins); Bordetella spp, including *B. pertussis* (for example pertactin, *pertussis* toxin or derivatives thereof, filamenteous hemagglutinin, adenylate cyclase, fimbriae), *B. parapertussis* and *B. bronchiseptica;* Mycobacterium spp., including *M. tuberculosis* (for example ESAT6, Antigen 85A, -B or -C), *M. bovis, M. leprae, M. avium, M. paratuberculosis, M. smegmatis;* Legionella spp, including *L. pneumophila;* Escherichia spp, including enterotoxic *E. coli* (for example colonization factors, heat-labile toxin or derivatives thereof, heat-stable toxin or derivatives thereof), enterohemorragic *E. coli,* enteropathogenic *E. coli* (for example shiga toxin-like toxin or derivatives thereof); Vibrio spp, including *V. cholera* (for example cholera toxin or derivatives thereof); Shigella spp, including *S. sonnei, S. dysenteriae, S. flexnerii;* Yersinia spp, including *Y. enterocolitica* (for example a Yop protein), *Y. pestis, Y. pseudotuberculosis;* Campylobacter spp, including *C. jejuni* (for example toxins, adhesins and invasins) and *C. coli;* Salmonella spp, including *S. typhi, S. paratyphi, S. choleraesuis, S. enteritidis;* Listeria spp., including *L. monocytogenes;* Helicobacter spp, including *H. pylori* (for example urease, catalase, vacuolating toxin); Pseudomonas spp, including *P. aeruginosa;* Staphylococcus spp., including *S. aureus, S. epidermidis;* Enterococcus spp., including *E. faecalis, E. faecium;* Clostridium spp., including *C. tetani* (for example tetanus toxin and derivative thereof), *C. botulinum* (for example botulinum toxin and derivative thereof), *C. difficile* (for example clostridium toxins A or B and derivatives thereof); Bacillus spp., including *B. anthracis* (for example botulinum toxin and derivatives thereof); Corynebacterium spp., including *C. diphtheriae* (for example diphtheria toxin and derivatives thereof); Borrelia spp., including *B. burgdorferi* (for example OspA, OspC, DbpA, DbpB), *B. garinii* (for example OspA, OspC. DbpA, DbpB), *B. afzelii* (for example OspA, OspC, DbpA, DbpB), B. andersonii (for example OspA, OspC, DbpA, DbpB), *B. hermsii;* Ehrlichia spp., including *E. equi* and the agent of the Human Granulocytic Ehrlichiosis; Rickettsia spp, including *R. rickettsii;* Chlamydia spp. including *C. trachomatis* (for example MOMP, heparin-binding proteins), *C. pneumoniae* (for example MOMP, heparin-binding proteins), *C. psittaci;* Leptospira spp., including *L. interrogans;* Treponema spp., including *T. pallidum* (for example the rare outer membrane proteins), *T. denticola, T. hyodysenteriae;* or derived from parasites such as Plasmodium spp., including *P. falciparum;* Toxoplasma spp., including *T. gondii* (for example SAG2, SAG3, Tg34); Entamoeba spp., including *E. histolytica;* Babesia spp., including *B. microti;* Trypanosoma spp., including *T. cruzi;* Giardia spp., including *G. lamblia;* Leshmania spp., including *L. major;* Pneumocystis spp., including *P. carinii;* Trichomonas spp., including *T. vaginalis;* Schisostoma spp., including *S. mansoni,* or derived from yeast such as Candida spp., including *C. albicans;* Cryptococcus spp., including *C. neoformans.*

Other preferred specific antigens for *M. tuberculosis* are for example Th Ra12, Tb H9, Tb Ra35, Tb38-1, Erd 14, DPV, MTI, MSL. mTTC2 and hTCC1 (WO 99/51748). Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd14-DPV-MTI, DPV-MTI-MSL, Erd14DPV-MTI-MSL-mTCC2, Erd14-DPV-MTI-MSL, DPV-MTI-MSL-mTCC2, TbH9-DPV-MTI (WO 99151748).

Most preferred antigens for Chlamydia include for example the High Molecular Weight Protein (HWMP) (WO 99/17741), ORF3 (EP 366 412), and putative membrane proteins (Pmps). Other Chlamydia antigens of the vaccine formulation can be selected from the group described in WO 99128475.

Preferred bacterial vaccines comprise antigens derived from Streptococcus spp, including *S. pneumoniae* (for example capsular polysaccharides and conjugates thereof, PsaA, PspA, streptolysin, choline-binding proteins) and the protein antigen Pneumolysin (Biochem Biophys Acta, 1989, 67, 1007; Rubins et al., Microbial Pathogenesis, 25, 337–342), and mutant detoxified derivatives thereof (WO 90/06951; WO 99/03884). Other preferred bacterial vaccines comprise antigens derived from Haemophilus spp., including *H. influenzae* type B (for example PRP and conjugates thereof), non typeable *H. influenzae*, for example OMP26, high molecular weight adhesins, P5, P6, protein D and lipoprotein D, and fimbrin and fimbrin derived peptides (U.S. Pat. No. 5,843,464) or multiple copy varients or fusion proteins thereof.

Derivatives of Hepatitis B Surface antigen are well known in the art and include, inter alia, those PreS1, Pars2 S antigens set forth described in European Patent applications EP-A414 374; EP-A-0304 578, and EP 198474. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In a preferred embodiment of the present invention vaccines containing the claimed adjuvant comprise antigen derived from the Human Papillona Virus (HPV) considered to be responsible for genital warts (HPV 6 or HPV 11 and others), and the HPV viruses responsible for cervical cancer (HPV16, HPV18 and others).

Particularly preferred forms of genital wart prophylactic, or therapeutic, vaccine comprise L1 particles or capsomers, and fusion proteins comprising one or more antigens selected from the HPV 6 and HPV 11 proteins E6, E7, L1, and L2.

The most preferred forms of fusion protein are: L2E7 as disclosed in WO 96/26277, and proteinD(1/3)-E7 disclosed in GB 9717953.5 (PCT/EP98/05285).

A preferred HPV cervical infection or cancer, prophylaxis or therapeutic vaccine, composition may comprise HPV 16 or 18 antigens. For example, L1 or L2 antigen monomers, or L1 or L2 antigens presented together as a virus like particle (VLP) or the L1 alone protein presented alone in a VLP or caposmer structure. Such antigens, virus like particles and capsomer are per se known. See for example WO94/00152, WO94/20137, WO94/05792, and WO93/02184.

Additional early proteins may be included alone or as fusion proteins such as E7, E2 or preferably F5 for example; particularly preferred embodiments of this includes a VLP comprising L1E7 fusion proteins (WO 96/11272).

Particularly preferred HPV 16 antigens comprise the early proteins E6 or F7 in fusion with a protein D carrier to form Protein D-E6 or E7 fusions from HPV 16, or combinations thereof; or combinations of E6 or E7 with L2 (WO 96/26277).

Alternatively the HPV 16 or 18 early proteins E6 and E7, may be presented in a single molecule, preferably a Protein D-E6/E7 fusion. Such vaccine may optionally contain either or both E6 and E7 proteins front HPV 18, preferably in the form of a Protein D-E6 or Protein D-E7 fusion protein or Protein D E6/E7 fusion protein.

The vaccine of the present invention may additionally comprise antigens from other HPV strains, preferably from strains HPV 31 or 33.

Vaccines of the present invention further comprise antigens derived from parasites that cause Malaria. For example, preferred antigens from *Plasmodia falciparum* include RTS,S and TRAP. RTS is a hybrid protein comprising substantially all the C-terminal portion of the circumsporozoite (CS) protein of *P.falciparum* linked via four amino acids of the preS2 portion of Hepatitis B surface antigen to the surface (S) antigen of hepatitis B virus. It's full structure is disclosed in the International Patent Application No. PCT/EP92/02591, published under Number WO 93/10152 claiming priority from UK patent application No.9124390.7. When expressed in yeast RTS is produced as a lipoprotein particle, and when it is co-expressed with the S antigen from HBV it produces a mixed particle known as RTS,S. TRAP antigens are described in the International Patent Application No. PCT/GB89/00895. published under WO 90/01496. A preferred embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in Plasmodium spp.

The formulations may also contain an anti-tumour antigen and be useful for the immunotherapeutic treatment of cancers. The formulations may also contain an anti-tumour antigen and be useful for the immunotherapeutic treatment of cancers. For example, the adjuvant formulation finds utility with tumour rejection antigens such as those for prostrate, breast, colorectal, lung, pancreatic, renal or melanoma cancers. Exemplary antigens include MAGE 1, 3 and MAGE 4 or other MAGE antigens such as disclosed in WO99/40188, PRAME, BAGE, Lage (also known as NY Eos 1) SAGE and HAGE (WO 99/53061) or GAGE (Robbins and Kawakami, 1996. Current Opinions in Immunology 8, pps 628–636; Van den Eynde et al., International Journal of Clinical & Laboratory Research (submitted 1997); Correale et al. (1997), Journal of the National Cancer Institute 89, p293. Indeed these antigens are expressed in a wide range of tumour types such as melanoma, lung carcinoma, sarcoma and bladder carcinoma.

MAGE antigens for use in the present invention may be expressed as a fusion protein with an expression enhancer or an Immunological fusion partner. In one embodiment of the present invention, the derivative is a fusion proteins comprising an antigen from the MAGE protein family linked to a heterologous partner. For example MAGE 3. The proteins may be chemically conjugated, but are preferably expressed as recombinant fusion proteins allowing increased levels to be produced in an expression system as compared to non-fused protein. Thus the fusion partner may assist in providing T helper epitopes(immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

In a preferred form of the invention, the immunological fusion partner is derived from protein D, a surface protein of the gram-negative bacterium, Haemophilus influenza B (WO91 /18926). Preferably the protein D derivative comprises approximately the first 1/3 of the protein, in particular approximately the first N-terminal 100–110 amino acids. Preferably the protein D derivative is lipidated. Preferably the first 109 residues of the Lipoprotein D fusion partner is included on the N-terminals to provide the vaccine candidate antigen with additional exogenous T-cell epitopes and increase expression level in *E-coli* (thus acting also as an expression enhancer). The lipid tail ensures optimal presentation of the antigen to antigen presenting cells.

Other fusion partners include the non-structural protein from influenzae virus, NS1 (hemagglutinin). Typically the N terminal 81 amino acids are utilised, although different fragments may be used provided they include T-helper epitopes.

In another embodiment the immunological fusion partner is the protein known as LYTA. Preferably the C terminal portion of the molecule is used. Lyta is derived from Streptococcus pneumoniae which synthesize an N-acetyl-L-alanine amidase, amidase LYTA, (coded by the lytA gene {Gene, 43 (1986) page 265–272} an autolysin that specifically degrades certain bonds in the peptidoglycan backbone The C-terminal domain of the LYTA protein is responsible for the affinity to the choline or to some choline analogues such as DEAF. This property has been exploited for the development of *E.coli* C-LYTA expressing plasmids useful for expression of fusion proteins. Purification of hybrid proteins containing the C-LYTA fragment at its amino terminus has been described {Biotechnology: 10, (1992) page 795–798}. As used herein a preferred embodiment utilises the repeat portion of the Lyta molecule found in the C terminal end starting at residue 178. A particularly preferred form incorporates residues 188–305.

The immunological fusion partners noted above are also advantageous in aiding expression. In particular, such fusions are expressed at higher yields than native recombinant MAGE proteins. Such constructs are disclosed in Wo99/40188.

Other tumour-specific antigens are suitable for use with the adjuvants of the present invention and include, but are not restricted to tumour-specific gangliosides such as GM 2, and GM3 or conjugates thereof to carrier proteins; or said antigen may be a self peptide hormone such as whole length Gonadotrophin hormone releasing hormone (GnRH, WO 95/20600), a short 10 amino acid long peptide, useful in the treatment of many cancers, or in immunocastration.

In a preferred embodiment prostate antigens are utilised, such as Prostate specific antigen (PSA), PAP, PSCA (PNAS 95(4) 1735–1740 1998), PSMA or, in a preferred embodiment an antigen known as Prostase.

Prostase is a prostate-specific serine protease (trypsin-like), 254 amino acid-long, with a conserved serine protease catalytic triad H-D-S and a amino-terminal pre-propeptide sequence, indicating a potential secretory function (P. Nelson, Lu Gan, C. Ferguson, P. Moss, R. Gelinas, L. Hood & K. Wand, "Molecular cloning and characterisation of prostase, an androgen-regulated serine protease with prostate restricted expression, In Proc. Natl. Acad. Sci. USA (1999) 96, 3114–3119). A putative glycosylation site has been described. The predicted structure is very similar to other known serine proteases, showing that the mature polypeptide folds into a single domain. The mature protein is 224 amino acids-long, with one A2 epitope shown to be naturally processed.

Prostase nucleotide sequence and deduced polypeptide sequence and homologs are disclosed in Ferguson, et al. (Proc. Natl. Acad. Sci. USA 1999. 96, 3114–3119) and in International Patent Applications No. WO 98/12302 (and also the corresponding granted patent U.S. Pat. No. 5,955, 306). WO 98/20117 (and also the corresponding granted pass U.S. Pat. Nos. 5,840,871 and 5,786,148) (prostate-specific kallikrein) and WO 00/04149 (P703P).

The present invention provides formulations comprising prostase protein fusions based on prostase protein and fragments and homologues thereof ("derivatives").

Such derivatives are suitable for use in therapeutic vaccine formulations which are suitable for the treatment of a prostate tumours. Typically the fragment will contain at least 20, preferably 50. more preferably 100 contiguous amino acids as disclosed in the above referenced patent and paten applications. In one embodiment there is provided a mutated prostase antigen wherein the mutation occurs in the active site of the protein. The prostase antigen derivative or fragments and homologues thereof carry a mutation in the active site of the protein, to reduce substantially or preferably eliminate its protease biological activity. Preferred mutations involve replacing the Histidine and Aspartate catalytic residues of the serine protease. In a preferred embodiment, prostase contains a Histidine-Alanine mutation in the active site, for example at residue 71 of prostate sequence (Ferguson, et al. (Proc. Natl. Acad. Sci. USA 1999, 96, 3114–3119). Corresponding mutation in homologous proteins are expressly contemplated. For example this mutation corresponds to position 43 in P703P This mutation can lead to a significant decrease in the catalytic efficiency (expressed in enzymatic specific activity) of the protein. Preferably the reduction in the catalytic efficiency is at least by a factor of $10^3$, more preferably at least by a factor of $10^6$. The protein which has undergone a histidine alanine mutation is hereafter referred to as*(star).

In one embodiment, the Prostase either mutated or non mutated is part of a fusion protein, comprising the tumour-associated prostase or fragment or humologues thereof and a heterologous protein or part of a protein acting as a fusion partner. The protein and the fusion partner may be chemically conjugated, but are preferably expressed as recombinant fusion proteins in a heterologous expression system.

In a preferred embodiment of the invention there is provided a prostase fusion protein or fragment or homologues thereof linked to an immunological fusion partner that may assist in providing T helper epitopes. Thus the fusion partner may act through a bystander helper effect linked to secretion of activation signals by a large number of T cells specific to the foreign protein or peptide, thereby enhancing the induction of immunity to the prostase component as compared to the non-fused protein. Preferably the heterologous partner is selected to be recognizable by T cells in a majority of humans.

In another embodiment, tie invention provides a prostase protein or fragment or homologues thereof linked to a fusion partner that acts as an expression enhancer. Thus the fusion partner may assist in aiding in the expression of prostase in a heterologous system, allowing increased levels to be produced in an expression system as compared to the native recombinant protein.

Preferably the fusion partner will be both an immunological fusion partner and an expression enhancer partner. Accordingly, the present invention provides fusion proteins comprising a mutated tumour-specific prostase or a fragment thereof linked to a fusion partner. Preferably the fusion partner is acting both as an immunological fusion partner and as an expression enhancer partner. Accordingly, in a preferred form of the invention, the fusion partner is the non-structural protein from influenzae virus, NS) (hemagglutinin) or fragment thereof, Typically the N-terminal 81 amino acids are utilised, although different fragments may be used provided they include T-helper epitopes (C. Hackett, D. Horowitz, M. Wysocka & S. Dillon, 1992, J. Gen. Virology, 73, 1339–1343). When NS1 is the immunological fusion partner it has the additional advantage in that it allows higher expression yields to be achieved. In particular, such fusions are expressed at higher yields than the native recombinant prostase proteins.

In a most preferred embodiment, the fusion protein comprises the N-terminal 81 amino acids of NS1 non structural protein fused to the 5 to 226 carboxy-terminal amino acids of P703P.

A further preferred prostate antigen is known as P501S, sequence ID no 113 of Wo98/37814. Immunogenic fragments and portions thereof comprising at least 20, preferably 50, more preferably 100 contiguous amino acids as disclosed in the above referenced patent application. See for example PS108 (WO 98/50567).

Other prostate specific antigens are known from Wo98137418, and WO/004149. Another is STEAP PNAS 96 14523 14528 7–12 1999.

Other tumour associated antigens useful in the context of the present invention include: Plu -1 J Biol. Chem 274 (22) 15633–15645, 1999, HASH -1, HasH-2, Cripto (Salomon et al Bioessays 199, 21 61 –70,U.S. Pat. No. 5,654,140) Criptin U.S. Pat. No. 5,981,215. Additionally, antigens particularly relevant for vaccines in the therapy of cancer also comprise tyrosinase and survivin.

Mucin dervied peptides such as Muc1 see for example U.S. Pat. Nos. 5,744,144, 5,827,666 WO 8805054, U.S. Pat. No. 4,963,484. Specifically contemplated are Muc 1 derived peptides that comprise at least one repeat unit of the the Muc 1 peptide, preferably at least two such repeats and which is recognised by the SM3 antibody (U.S. Pat. No. 6,054,438). Other mucin derived peptides include peptide from Muc 5.

The present invention is also useful in combination wide breast cancer antigens such as her 2/ Neu, mammaglobin (U.S. Pat. No. 5,668,267) or those disclosed in WO/00 52165, WO99/33869, WO99/19479, WO 98/45328. Her 2 neu antigens are disclosed inter alia, in U.S. Pat. No. 5,801,005. Preferably the Her 2 neu comprises the entire extracellular domain (comprising approximately amino acid 1–645) or fragmants thereof and at least an immunogenic portion of or the entire intracellular domain approximately the C terminal 580 amino acids. In particular, the intracellular portion should comprise the phosphorylation domain or fragments thereof. Such constructs are disclosed in WO00/44899. A particularly preferred construct is known as ECD PD a second is known as ECD ΔPD See Wo/00/44899.

The her 2 neu as used herein can be derived from rat, mouse or human.

The Her2-neu antigen may be the entire Her2-neu antigen or portions thereof. Preferred portions comprises the extracellular domain. In a more preferred embodiment there is provided an fusion protein comprising an extracellular domain linked to a portion of the intracellular domain as disclosed in WO 00/44899.

The present invention is directed to formulations capable of modulating, preferably eliciting or enhancing, immunity to the protein product of HER-2/neu oncogene expression, including for malignancies in a warm-blooded animal where an s amplified HER-2/neu gene with a malignancy does not require that the protein expression product of the gene be present on the tumour. For example, overexpression of the gene may be involved with initiation and early stages of tumour formation, but the protein expression may subsequently be reduced or absent. The present invention may be used to elicit or enhance an effective immune response to convert a HER-2/neu positive tumour to HER-2/neu negative, in addition to preventing the establishment of HER-2/neu positive tumours and provoking the regression of existing HER-2/neu positive tumours.

The following abbreviations are used throughout the specification: "ECD" refers to the extracellular domain, "ICD" refers to the intracellular domain, "PD" refers to the phosphorylation domain (ie, the domain that is phosphorylated) that is within the intracellular domain, "ΔPD" refers to a fragment of the phosphorylation domain that is within the phosphorylation domain, and "KD" refers to the kinase domain that is within the intracellular domain. The product of expression of the HER-2/neu gene is referred to herein as the "HER-2/neu protein," also known and referred to as "p185" or "c-erbB2".

The "HER-2/neu ECD-ICD fusion protein," also referred to herein as "ECD-ICD" or "ECD-ICD fusion protein," refers to a fusion protein (or fragments thereof) comprising the extracellular domain (or fragments thereof) and the intracellular domain (or fragments thereof) of the HER-21neu protein. These represent preferred antigens to utilise in the context of the present invention. As used herein, the ECD-ICD fusion protein does not include a substantial portion of the HER-2/neu transmembrane domain, and preferably does not include any of the HER-2/neu transmembrane domain.

The "HER-2/neu ECD-PD fusion protein,>also referred to as "ECD-PD" or "ECD-PD fusion protein," or the "HER-2/neu ECD-ΔPD fusion protein," also referred to as "ECD-ΔPD" or ECD-ΔPD fusion protein," refer to fusion proteins (or fragments thereof) comprising the extracellular domain (or fragments thereof) and phosphorylation domain (or fragments thereof, eg, ΔPD) of the HER-2/neu protein. The ECD-PD and ECD-ΔPD fusion proteins do not include a substantial portion of the HER-2/neu transmembrane domain, and preferably do not include any of the HER-2/neu transmembrane domain.

The terms "HER-2/neu ECD-ICD fusion protein" and "HER-2/neu ECD-PD fusion protein" and their related terms are also understood to refer to fragments thereof, homologs therefore and functional equivalents thereof (collectively referred to as "variants"), such as those in which one or more amino acids which, in preferred embodiments of the invention, either (i) increase the elicitation or enhancement of an immune response as compared to the HER-2/neu protein, or (ii) do not substantially affect elicitation or enhancement of an immune response as compared to the HER-2/neu protein (eg variant stimulates a response by helper T cells or cytotoxic T cells or stimulates the production of antibodies). Specific, non-limiting, examples of variants including exemplary fragments, homologs and functional equivalents of the HER-2/neu ECD-ICD fusion protein and HER-2/neu ECD-PD fusion protein are described in more detail herein. Variants can be "substantially identical" or "substantially similar" to a fusion protein comprising native polypeptide components, and retain the ability to stimulate an immune response.

The HER-2/neu PD is 268 amino acids in length, is intracellular, and can be phosphorylated by protein tyrosine kinases. The region shares no identity with the corresponding part of other tyrosine kinase receptors. Thus, the specificity and uniqueness of this domain makes it particularly preferred for use as a tumour vaccine. However, the expression of this domain alone in bacterial and mammalian cells is problematic. For example, the resultant PD protein is very labile and is not appropriate for large scale production. In one embodiment, this invention thus preferably utilises a fusion comprising all or part of the intracellular domain or the phosphorylation domain to all or part of the HER-2/neu extracellular domain. The ECD-ICD fusion proteins and the ECD-PD fusion proteins of the invention are soluble. are secreted and are stable in culture media.

The vaccines of the invention will be useful against any cancer characterised by tumour associated antigen expresion, such as HER-2/neu expression. In addition to allowing increased expression of the intracellular domain or phosphorylation domain, or variants thereof, as a fusion protein with the extracelluar domain or its variants, the ECD-ICD and ECD-PD fusion proteins provide for an improved vaccine formulation.

The formulations may contain antigens associated with tumour-support mechanisms (e.g. angiogenesis, tumour invasion) for example tie 2, VEGF.

Accordingly the present invention provides in an embodiment, a vaccine formulation comprising an adjuvant composition, said adjuvant comprising a saponin and a immunostimulatory oligonucleotide and a tumour associated or tissue specific antigen. In a preferred embodiment, the adjuvant additionally comprises a lipopolysaccharide.

It is foreseen that compositions of the present invention will be used to formulate vaccines containing antigens derived from Borrelia sp. For example, antigens may include nucleic acid, pathogen derived antigen or antigenic preparations, recombinantly produced protein or peptides, and chimeric fusion proteins. In particular the antigen is OspA. The OspA may be a full mature protein in a lipidated form virtue of the host cell (*E.Coli*) termed (Lipo-OspA) or a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

Vaccines of the present invention may be used for the prophylaxis or therapy of allergy. Such vaccines would comprise allergen specific (for example Der p1) and allergen non-specific antigens (for example peptides derived from human IgE, including but not restricted to the stanworth decapeptide (EP 0 477 231 B1)).

Vaccines of the present invention may also be used for the prophylaxis or therapy of chronic disorders others than allergy, cancer or infectious diseases. Such chronic disorders are diseases such as atherosclerosis, and Alzheimer.

Antigens relevant for the prophylaxis and the therapy of patients susceptible to or suffering from Alzheimer neurodegenerative disease are, in particular, the N terminal 39–43 amino acid fragment (Aβ) of the amyloid precursor protein and smaller fragments. This antigen is disclosed in the International Patent Application No. WO 99127944— (Athena Neurosciences).

The amount of protein in each vaccine dose is selected as an amount which induces an immunoprotective response without significant, adverse side effect in typical vaccinees. Such amount will vary depending upon which specific immunogen is employed and how it is presented. Generally, it is expected that each dose will comprise 1–1000 μg of protein, preferably 1–500 μg, preferably 1–100 μg, most preferably 1 to 50 μg An optimal amount for a particular vaccine can be ascertained by standard studies involving observation of appropriate immune responses in vaccinated subjects Following an initial vaccination, subjects may receive one or several booster immunisation adequately spaced. Such a vaccine formulation may be applied to a mucosal surface of a mammal in either a priming or boosting vaccination regime; or alternatively be administered systemically, for example via the transdermal, subcutaneous or intramuscular routes.

The amount of CpG or immunostimulatory oligonucleotides in the adjuvants or vaccines of the present invention is generally small, but depending on the vaccine formulation may be in the region of 1–1000 g per dose, preferably 1–500 g per dose, and more preferably between 1 to 100 g per dose.

The amount of saponin for use in the adjuvants of the present invention may be in the region of 1–1000 g per dose, preferably 1–500 g per dose, more preferably 1–250 g per dose, and most preferably between 1 to 100 g per dose. The ratio of CpG:saponin (w/w) will, therefore, be in the range of 1:1000 to 1000:1, and will typically be in the range of 1:100 to 100:1, and preferably in the range of 1:10 to 1:1 or 1:1 to 10:1, and most preferably 1:1, 4:1 or 10:1.

The formulations of the present invention maybe used for both prophylactic and therapeutic purposes. Accordingly, there is provided the use of a combination of a saponin and a CpG molecule in the manufacture of a vaccine for the prophylaxis and the treatment of viral, bacterial, parasitic infections, allergy, cancer and other non-chronic disorders. Accordingly, the present invention provides for a method of treating a mammal susceptible to or suffering from an infectious disease or cancer, or allergy, or autoimmune disease. In a further aspect of the present invention there is provided a vaccine or adjuvant combination, comprising a saponin and CpG, as herein described for use as a medicament. Vaccine preparation is generally described in New Trends and Developments in Vaccines, edited by Voller et al., University Park Press, Baltimore, Md., U.S.A. 1978.

It is foreseen that compositions of tie present invention will be used to formulate vaccines containing antigens derived from a wide variety of sources. For example, antigens may include human, bacterial, or viral nucleic acid, pathogen derived antigen or antigenic preparations, tumour derived antigen or antigenic preparations, host-derived antigens, including peptides derived from IgE, such as the histamine releasing decapeptide of IgE (known as the Stanworth decapeptide), recombinantly produced protein or peptides, and chimeric fusion proteins.

There is provided by the present invention a systemic vaccine composition comprising an antigen, a saponin and an immunostimulatory oligonucleotide.

Accordingly, there is provided a method of treatment of an individual susceptible to or suffering from a disease by the administration of a composition as substantially described herein through the systemic route of said individual. Also provided is a method to prevent an individual from contracting a disease selected from the group comprising infectious bacterial and viral diseases, parasitic diseases, prostate, breast, colorectal, lung, pancreatic, renal, ovarian or melanoma cancers; non-cancer chronic disorders, allergy, Alzheimer, atherosclerosis, comprising the administration of a composition as substantially described herein through the systemic route of said individual.

Alternatively, there is provided by the present invention a mucosal vaccine composition comprising an antigen, and a haemolytic saponin. Accordingly. there is provided a method of treatment of an individual susceptible to or suffering from a disease by the administration of a composition as substantially herein described to a mucosal surface of said individual.

Furthermore, there is described a method of inducing a systemic antigen specific immune response in a mammal, comprising administering to a mucosal surface of said mammal a composition comprising an antigen and a haemolytic saponin. Further there is provided a method of manufacture of a vaccine or adjuvant are also provided, comprising taking a saponin and taking a CpG molecule and admixing them with an antigen.

Examples of suitable pharmaceutically acceptable excipients for use in the combinations of the present invention include water, phosphate buffered saline, isotonic buffer solutions.

FIGURE LEGENDS

FIG. 1: OspA specific IgG titres 14 days after the nasal boosting.

FIG. 2: OspA specific LA2 titres 14 days after the nasal boosting.

FIG. 3: serum Flu strain specific IgG titres 14 days after the nasal boosting.

FIG. 4: serum Flu strain specific serum HemAgglutination Inhibition (HAI) titres 14 days after the nasal boosting.

FIG. 5: OspA specific LA2 titres in mice

FIG. 6: gp120-specific lymphoproliferation activity of spleen cells from immunized mice. The antigen-specific activity is expressed as SI for different antigen concentrations for all 4 experimental groups.

FIG. 7: HBsAg-specific CTL activity of spleen cells from immunized mice. Effector cell activity was assessed by examining $^{51}$Cr release of P815 cells (open circles) or s-transfected P815 cells (closed circles).

FIG. 8: HBsAg-specific antibody responses in immunized mice. Specific antibody titers (expressed as EU/ml) and isotype profiles were evaluated using ELISA tests. Values from pooled sera are shown in the table, and isotype distributions are also depicted in a graphic.

FIG. 9: HBSAg- and gp120specific lymphoproliferation activity of spleen cells from immunized mice. The antigen-specific activity is expressed as SI for different antigen concentrations for all 4 experimental groups.

FIG. 10: HBsAg- and gp120-specific CTL activity of spleen cells from immunized mice. Effector cell activity was assessed by examining $^{5}$Cr release of control P815 cells (open symbols) or P815 cells displaying an HBsAg or gp120 CTL epitope (closed symbols).

FIG. 11: Gp120 specific and HbsAg-specific antibody responses in immunized mice. Specific antibody titers (expressed in μg/ml) (FIG. 11A) and isotype profiles were evaluated using ELISA tests. Values from pooled sera are shown in the table, and isotype distributions are also depicted in a graphic. FIG. 11B shows the isotype pattern of gp120-specific antibodies.

FIG. 12: Evolution of the mean tumour growth per groups of 10 animals over time.

The present invention is illustrated by, but not restricted to, the following examples.

EXAMPLE 1

The Use of QS21 and CpG for the Intranasal Boosting of Systemic Antibodies to Lipo-OspA In this example we investigated whether lytic saponins such as QS21 and immunostimulants such as CpG were able to enhance in a synergistic fashion systemic immunological responses to an intranasal boosting vaccination of mice. Female Balb/c mice (5 animals per group), aged 8 weeks, were immunized intramuscularly with lipo-OspA (lug) formulated onto alum (50 μg). After 3 months, the mice were boosted intranasally (under anesthesia) with 10 μl of solution (5 μl per nostril, delivered as droplets by pipette) containing 5 μg lipo-OspA in either A: PBS; B: 20 μg CpG 1001 (TCC ATG AGC TTC CTG ACG TT, Krieg 1826); C: 5 μg QS21 (obtained from Cambridge Biotech, USA); D: 20 μg CpG 1001+5 μg QS21; or, E: by intra muscular injection of 1 μg lipo-OspA adsorbed onto alum (50 μg).

FIGS. 1 and 2 show the OspA specific IgG titres and LA2 titres 14 days after the nasal boosting.

Methods

ELISA for the Measurement of OspA-specific Serum IgG in Mice

Maxisorp Nunc immunoplates are coated overnight at 4° C. with 50 μl/well of 1 μg/ml OspA diluted in PBS (in rows B to H of plate), or with 50 μl of 5 μg/ml purified goat anti-mouse Ig (Boerhinger), in PBS (row A). Free sites on the plates are blocked (1 hour, 37° C.) using saturation buffer PBS containing 1%BSA, 0.1% polyoxyethylene sorbitan monolaurate (TWEEN 20), and 4% Normal Bovine Serum (NBS). Then, serial 2-fold dilutions of IgG isotype mixture, diluted in saturation buffer (50 μl per well) and added as a standard curve (mixture of mouse monoclonal antibodies IgG1, IgG2 and IgG2b from Sigma, starting at 200 ng/ml and put in row A), and serum samples (starting at a 1/100 dilution and put in rows B to H) are incubated for 1 hr 30 mins at 37° C. The plates are then washed (×3) with washing buffer (PBS, 0.1% polyoxyethylene sorbitan monolaurate (TWEEN 20)). Then. biotinylated goat anti-mouse IgG (Amersham) diluted 1/5000 in saturation buffer are incubated (50 μl/well) for 1 hr 30 mins, at 37° C. After 3 washings, and subsequent addition of streptavidin-horseradish peroxidase conjugate (Amersham), plates are washed 5 times and incubated for 20 min at room temperature with 50 μl/well of revelation buffer (OPDA 0.4 mg/ml (Sigma) and $H_2O_2$ 0.03% in 50 mM pH 4.5 citrate buffer). Revelation is stopped by adding 50 μl/well $H_2SO_4$2N. Optical densities are read at 492 and 630 nm by using Biorad 3550 immunoreader. Antibody titers are calculated by the 4 parameter mathematical method using SoftMaxPro software.

Inhibition Assay for the Measurement of Serum LA2-like Antibody titres to lipo-OspA Antibody titres in the vaccinees were studied with respect to their LA2-like specificity. LA2 is a murine monoclonal antibody which recognizes a conformational OspA epitope at the surface of the bacteria and has been shown to be able to kill B. burgdorferi in vitro, as well as to protect mice against a challenge with laboratory-grown spirochete (Schaible UE et al. 1990. Proc Natl Acad Sci USA 87:3768–3772). Moreover, LA-2 mab has been shown to correlate with bactericidal antibodies, and studies on human sera showed also a good correlation between the total anti-OspA IgG titers and the LA-2 titers (as measured by ELISA). Maxisorp Nunc immunoplates are coated overnight at 4° C. with 50 μl/well of 0.5 μg/ml lipo OspA diluted in PBS. Free sites were blocked with saturation buffer for 1 hr at 37° C. with (100 μl/well of saturation. buffer: PBS/BSA 1%/Tween 20 0.1%/NBS 4%). Serial 2-fold dilutions of LA2 monoclonal Ab (mAb) starting at 4 μg/mi were diluted in saturation buffer (50 μl per well) to form a standard curve. Dilutions of serum samples from the vaccinees (starting at a 1/10 dilution) were also added and the plates incubated for 2 hrs at 37° C. The plates were washed after incubation 3 times with PBS/ TWEEN 20 (0.1%). LA2 mAb-peroxidase conjugate (1/10,000) diluted in saturation buffer was added to each well (50 µl/well) and incubated for 1 hr at 37° C. After 5 washings, plates are incubated for 20 min at room temperature (in darkness) with 50 µl/well of revelation buffer (OPDA 0.4 mg/ml and $H_2O_2$ 0.03% in 50 mM pH 4.5 citrate buffer). The reaction and colour formation was stopped with $H_2SO_4$ 2N. Optical densities are read at 492 and 630 mm by using Biorad 3550 immunoreader. LA2-like Ab titers are calculated by the 4 parameter mathematical method using SoftMaxPro software. LA2-like antibody titres were determined by comparison with the standard curve.

Results

CpG as well as QS21 improve significantly the intranasal boosting of systemic antibodies to Lipo-OspA. Moreover, when both adjuvants are combined, a synergistic effect on those responses is clearly demonstrated, especially in term of LA2 antibodies. Humoral responses elicited in the presence of QS21 and CpG are significantly higher than those induced by the parenteral booster. Taken together, these results show clearly the potential of intranasal formulations combining a lytic saponin and an immunostimulant.

EXAMPLE 2

Synergistic Combination of QS21 and CpG for Enhancing the Intranasal Boosting of Systemic Antibodies to Influenza Virus In this example we investigated whether haemolytic saponins such as QS21 (sec example) and immunostimulants such as CpG were able to enhance in a synergistic fashion the intranasal boost of systemic antibodies in mice primed intranasally with inactivated whole influenza virus. Female Balb/c mice (10 animals per group), aged 8 weeks, were primed intranasally with β-propiolactone inactivated trivalent whole influenza virus (A/Beijing/262/95; A/Johannesburg/33/94; B/Panama/45/90; 5 µg HA/strain) for mimicking the natural priming occurring in humans. After 28 days, the mice were boosted intranasally (under anesthesia) with 20 µl of solution (10 µl per nostril, delivered as droplets by pipette) containing 1.5 µg HA/strain of β-propiolactone inactivated trivalent whole influenza virus (same strains as in the priming immunization) in either A: PBS; B: 50 µg CpG (TCG TCG TTT TGT CGT TTT GTC GTT, Krieg 2006); C: 4.5 µg QS21 (obtained from Cambridge Biotech, USA); D: 50 µg CPG+4.5 µg QS21; or, E: by intra muscular injection of 1.5 µg HA/strain of trivalent split influenza virus (same strains as in the priming immunization). Flu antigens were supplied by SSD GmBH manufacturer (Dresden, Germany).

Figure 3:
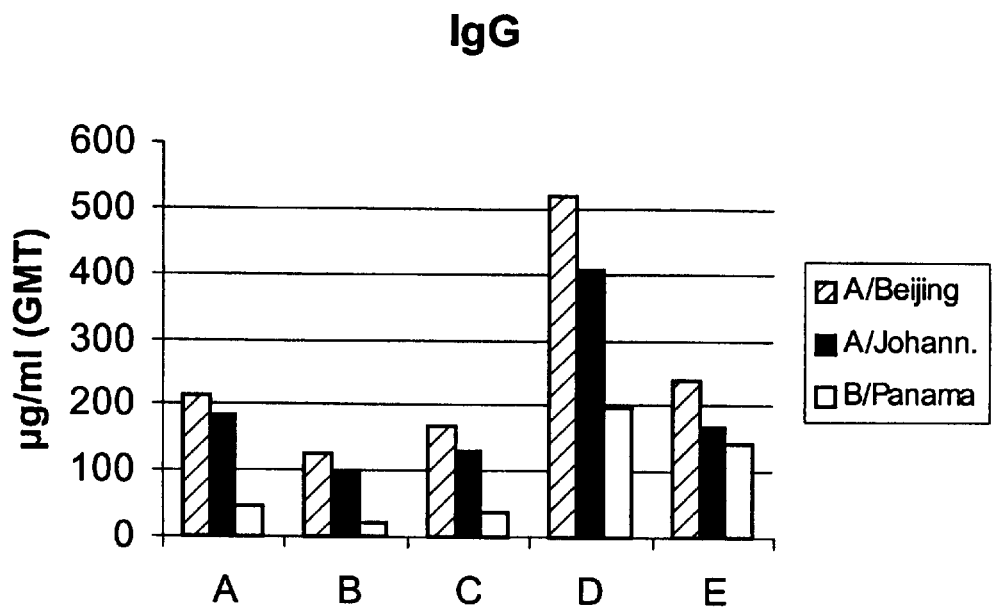
Figure 4:
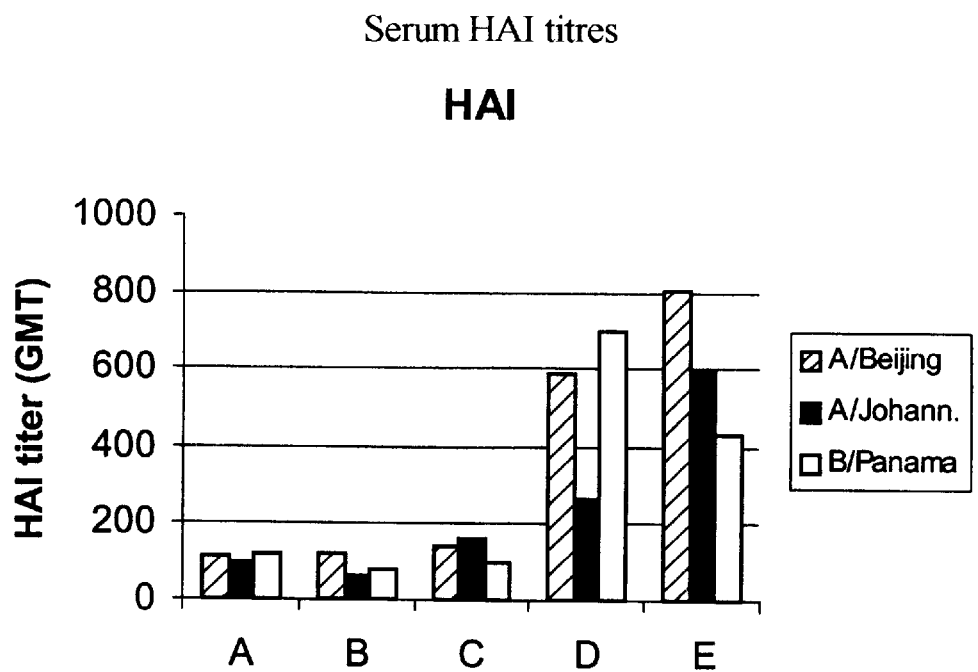

FIGS. 3 and 4 show the serum Flu strain specific IgG titres and HemAgglutination Inhibition (HAI) titres 14 days after the nasal boosting.

Methods

ELISA for the Measurement of Anti-influenza IgG Titres in Mice

Maxisorp Nunc immunoplates are coated overnight at 4° C. with 50 µl/well of 1 µg/ml whole influenza virus antigen diluted in PBS (in rows B to H of plate), or with 50 µl of 5 µg/ml purified goat anti-mouse Ig (Boerhinger), in PBS (row A). Free sites on the plates are blocked (1 hour, 37° C.) using saturation buffer: PBS containing 1% BSA, 0.1% polyoxyethylene sorbitan monolaurate (TWEEN 20), and 4% Normal Bovine Serum (NBS). Then, serial 2-fold dilutions of IgG isotype mixture, diluted in saturation buffer (50 µl per well) and added as a standard curve (mixture of mouse monoclonal antibodies IgG1, IgG2a and IgG2b from Sigma, starting at 200 ng/ml and put in row A), and serum samples (starting at a 1/100 dilution and put in rows B to H) are incubated for 1 hr 30 mins at 37° C. The plates are then washed (×3) with washing buffer (PBS, 0.1% polyoxyethylene sorbitan monolaurate (TWEEN 20)). Then, biotinylated goat anti-mouse IgG (Amersham) diluted 1/5000 in saturation buffer are incubated (50 µl/well) for 1 hr 30mins, at 37° C. After 3 washings, and subsequent addition of streptavidin-horseradish peroxidase conjugate (Amersham). plates are washed 5 times and incubated for 20 min at room temperature with 50 µl/well of revelation buffer (OPDA 0.4 mg/ml (Sigma) and $H_2O_2$ 0.03% in 50 mM pH 4.5 citrate buffer). Revelation is stopped by adding 50 µl/well $H_2SO_4$2N. Optical densities are read at 492 and 630 nm by using Biorad 3550 immunoreader. Antibody titers are calculated by the 4 parameter mathematical method using SoftMaxPro software.

The Whole influenza virus used for the coating (strain A/Beijing/262/95), inactivated with propiolactone (BPL), is supplied by SSD GmBH manufacturer (Dresden, Germany).

HemAgglutination Inhibition (HAI) Activity of Flu-specific Serum Abs in Mice

Sera (25 µ) are first treated for 20 minutes at room temperature (RT) with 100 µl borate 0.5M buffer (pH 9) and 125 µl Dade Behring-purchased kaolin. After centrifugation (30 minutes, 3000 RPM or 860 g), 100 µl supernatant (corresponding to a 1/10 dilution of the serum) are taken and incubated for 1 hour at 4° C. with 0.5% chicken red blood cells. Supernatant is collected after centrifugation for 10 minutes at 3200 RPM (970 g). Both operations are done for eliminating the natural hemagglutinating factors contained in the sera. Then, 25 µl treated-sera are diluted in 25 µl PBS (serial 2-fold dilutions starting at 1/20) in 96 well Greiner plates, BPL inactivated whole virus is added (25 µl/well) at a concentration of 4 Hemagglutination Units (i.e. at a dilution which is 4-fold lower than the last one provoking an agglutination of red blood cells) for 30 minutes at RT under agitation. Chicken red blood cells are then added (25 µl/well) for 1 hour at RT. Plates are finally kept overnight at 4° C. before to be read. The HAI titer corresponds to the last serum dilution inhibiting the virus-induced hemagglutination.

Results

CpG as well as QS21 do not improve the intranasal boosting of IgG or HAI antibodies to Flu strains. However, when both adjuvants are combined, a synergistic effect on those responses is clearly demonstrated. The HAI responses elicited in the presence of QS21 and CpG are even similar than those induced by the parenteral booster. These results confirm the potential of intranasal formulations combining a haemolytic saponin and an immunostimulant. They also show that several CpG sequences can be efficient in this context (Krieg 2006 in the present example and Krieg 1826 in the examples 3 and 5).

EXAMPLE 3

Figure 5:
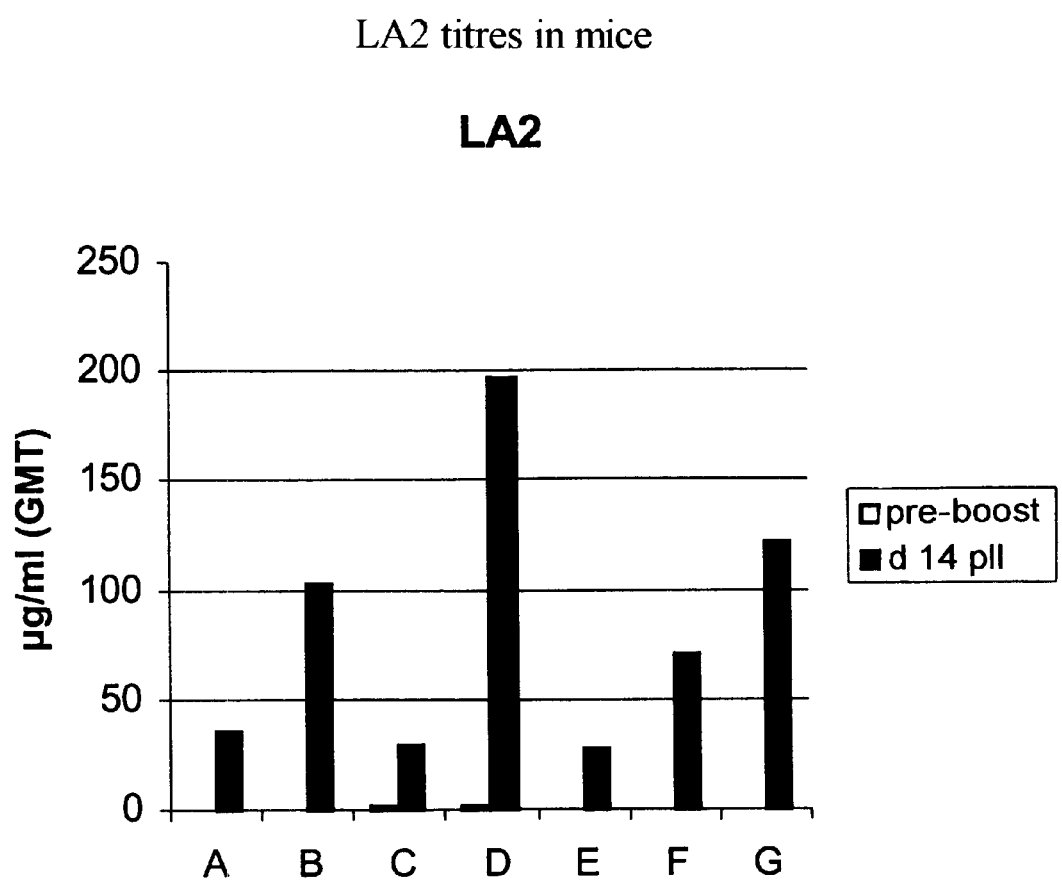

Synergistic Combination of –Escin and CpG for Enhancing the Intranasal Boosting of Systemic Antibodies to Lipo-OspA We assess in the present example the possibility that a synergy similar to that observed between QS21 and CpG could be obtained with other haemolytic saponins (see example) such as –Escin. The non haemolytic saponin, glycyrrhizic acid, is also tested. Female Balb/c mice (6 animals per group), aged 8 weeks, were primed itramuscularly with lipo-OspA (1 μg) formulated onto alum (50 μg). After 3 months, die mice were boosted intranasally (under anesthesia) with 10 μl of solution (5 μl per nostril, delivered as droplets by pipette) containing 5 μg lipo-OspA in either A: PBS; B: 50 μg CpG 1001 (TCC ATG AGC TTC CTG ACG TT, Krieg 1826); C: 5 μg β-Escin (purchased from Sigma); D: 50 μg CpG 1001+5 μg β-Escin; P: 5 μg glycyrrhizic acid (purchased from Sigma); F: 50 μg CpG 1001+5 μg glycyrrhizic acid or, G: by intra muscular injection of 1 μg lipo-OspA adsorbed onto alum (50 μg). FIG. 5 shows the OspA specific-LA2 titres 14 days after the nasal boosting.

Methods

The methods are the same as those detailed in Example 1.

Results

β-Escin and CpG act synergistically for enhancing the intranasal boosting of systemic LA2 Abs. This combination elicits more elevated Ab responses than the parenteral booster. On the other hand, such a synergy is not obtained by combining CpG with glycyrrhizic acid.

These results and the previous ones of this patent taken together show the ability of CpG and different haemolytic saponins to adjuvant immune responses in a synergistic fashion.

EXAMPLE 4

Immunogenicity Studies Using *P. falciparum* RTS.S and HIV-1 gp120 Formulated with CpG and/or DQS21

1. Experiment Outline

Two mouse immunogenicity studies were conducted to evaluate potential additive or synergistic effects of CpG oligonucleotides (CpG) and QS21. Groups of mice were immunized with RTS,S and gp120 formulated with CpG and QS21 alone or in combination. These adjuvant combinations were also tested in the presence of the carrier $Al(OH)_3$ or an oil-in-water (o/w) emulsion.

The immunogenicity of the formulations was examined after two parenteral immunizations. Sera were analyzed for the presence of antigen-specific antibodies, and for the distribution of antibody isotypes. Spleen cells were used to evaluate cell-mediated immune responses. Those cells were tested for the presence of cytotoxic T lymphocytes (CTL) and lymphoproliferative (lymphoproliferation) cells.

TABLE 1

Groups of mice in experiment 1

| Group | antigen | adjuvant |
| --- | --- | --- |
| 1 | RTS,S/gp120 | CpG/DQS21 |
| 2 | RTS,S/gp120 | DQS21 |
| 3 | RTS,S/gp120 | CpG/DQS21/Al(OH)$_3$ |
| 4 | RTS,S/gp120 | CpG/Al(OH)$_3$ |

TABLE 2

Groups of mice in experiment 2

| Group | antigen | adjuvant |
| --- | --- | --- |
| 1 | RTS,S/gp120 | CpG |
| 2 | RTS,S/gp120 | CpG/DQS21 |
| 3 | RTS,S/gp120 | CpG/QS21/o/w emulsion |

2. Formulation 2.1. Experiment 1

Formulation Process:

Formulations were prepared three days before each injection. When needed, RTS,S (10 μg) and gp 120 (10 μg) were adsorbed on 100 μg of $AL(OH)_3$. When needed, MPL (5 μg) was added and incubated 30 min before buffer addition as a mix of 10-fold concentrated PBS pH 7.4 and $H_2O$ excepted for the group without DQ for which the buffer was $PO_4$, NaCl 10/150 pH 6.8. After 30 min, it needed, QS21 (5 μg) mixed with liposomes in a weight ratio QS21/cholesterol of 1/5 (referred to as DQ) was added to the formulation. Thirty minutes later, for the formulations with the oligo, 100 μg of CpG was added 30 min prior addition of 50 μg/ml of thiomersal as preservative.

$Al(OH)_3$ + RTSS + gp120 - 1h - MPL - 30 min - premix - 30 min - DQ - 30 min - CpG - 30 min - Thio All incubations were carried out at room temperature with agitation.

2.2. Experiment 2

Formulation process:

Formulations are performed simultaneously for both injections. The volume of injection for one mouse is 100 μl. Fifty μg/ml of thiomersal is added as preservative.

Group 1: RTS,S (10 μg) and gp120 (10 μg) are diluted with $H_2O$ and PBS pH 6.8 for isotonicity. After 5 min., the formulation is adsorbed on CpG 1856 (100 μg).

Group 2: RTS,S (10 μg) and gp120 (10 μg) are diluted with $H_2O$ and PBS pH 7.4 for isotonicity. After 30 minutes RTS,S and gp120 are adsorbed on DQ (5 μg). After 30 min. of adsorption, the formulation is adsorbed on CpG 1856 (100 μg).

Group 3: RTS,S (10 μg) and gp120 (10 μg) are diluted with $H_2O$ and PBS pH 6.8 for isotonicity. After 5 min., the formulation is adsorbed on an o/w emulsion. After 5 min. of adsorption, the formulation is adsorbed on QS21 (5 μg) prior the addition of CpG (100 μg).

3. Immunological Methods

Nine (Balb/C×C57B1/6) F1 mice per group received into the bind footpads 2×50 μl vaccine twice at a two-week-interval. Two weeks later sera were obtained to assess antibody responses, and spleen cells were harvested to determine cell-mediated immune responses.

For lymphoproliferation analysis, cells were seeded in quadruplicates in 96-well round-bottomed microliter plates at a concentration of $2 \times 10^6$ per ml. Cells were cultured for 72 or 96 hrs in RPMI-1640 supplemented with antibiotics, glutamine and 1% (v/v) normal mouse serum in the presence of different concentrations of RTS,S or gp120 antigen. Control cells were cultured without antigen. Then the cells were pulsed overnight with 1 μCi/well [$^3$H]-thymidine, harvested and the incorporated radioactivity was determined in a beta-counter. Results are expressed as mean counts per minute (cpm).

For CTL analysis cells were cultured for 7 days in 6-well plates in the presence of 10 μg per ml of synthetic peptide pCM1003 (IPQSLDSWWTSL) corresponding to an HBsAg CTL epitope (Schirmbeck et al., 1995) or peptide pCM1007 (GIHIGPGRAFYAARK) representing an gp120 CTL epitope (Casement et al., 1995). At the end of the culture period effector cells were assessed in duplicate for HBsAg-specific cytolytic activity in standard [$^{51}$Cr]-release assays using control and S-transfected P815 cells. Gp120-specific cytotoxicity was determined by using P815 target cells that were either left untreated or pulsed for 1 hr with peptide pCM1007. Minimum and maximum release were determined with target cells without effector cells and by the addition of 3% (v/v) Triton X-100, respectively. Results are expressed as % [51Cr]-release (cpm of experimental culture—cpm of spontaneous release/cpm of maximum release—cpm of spontaneous release).

Titration and isotyping of pooled sera was performed in a standard enzyme-linked immunosorbent assay (ELISA) format using plates coated with HbsAg. Sera were diluted in PBS/BSA starting at 1:400. Biotinylated secondary antibodies specific for Ig or the isotypes IGg1, IgG2a and IgG2b followed by a horseradish peroxydase-streptavidin conjugate were used for detection of bound antibodies. ELISA titers were calculated from a reference by SoftmaxPro and expressed in ELISA units (EU/ml). Gp120-specific antibody titers were determined in a standard ELISA using plates coated with gp120 protein. Sera were diluted in PBS/Tween20/BSA starting at 1:100. Biotinylated secondary antibodies specific for Ig or the isotypes IgG1, IgG2a and IgG2b followed by a horseradish peroxydase-streptavidin conjugate were used for detection of bound antibodies. Titers were calculated in relative to a standard mouse Ig and expressed as µg/ml.

4. Results

Experiment 1

Figure 6:
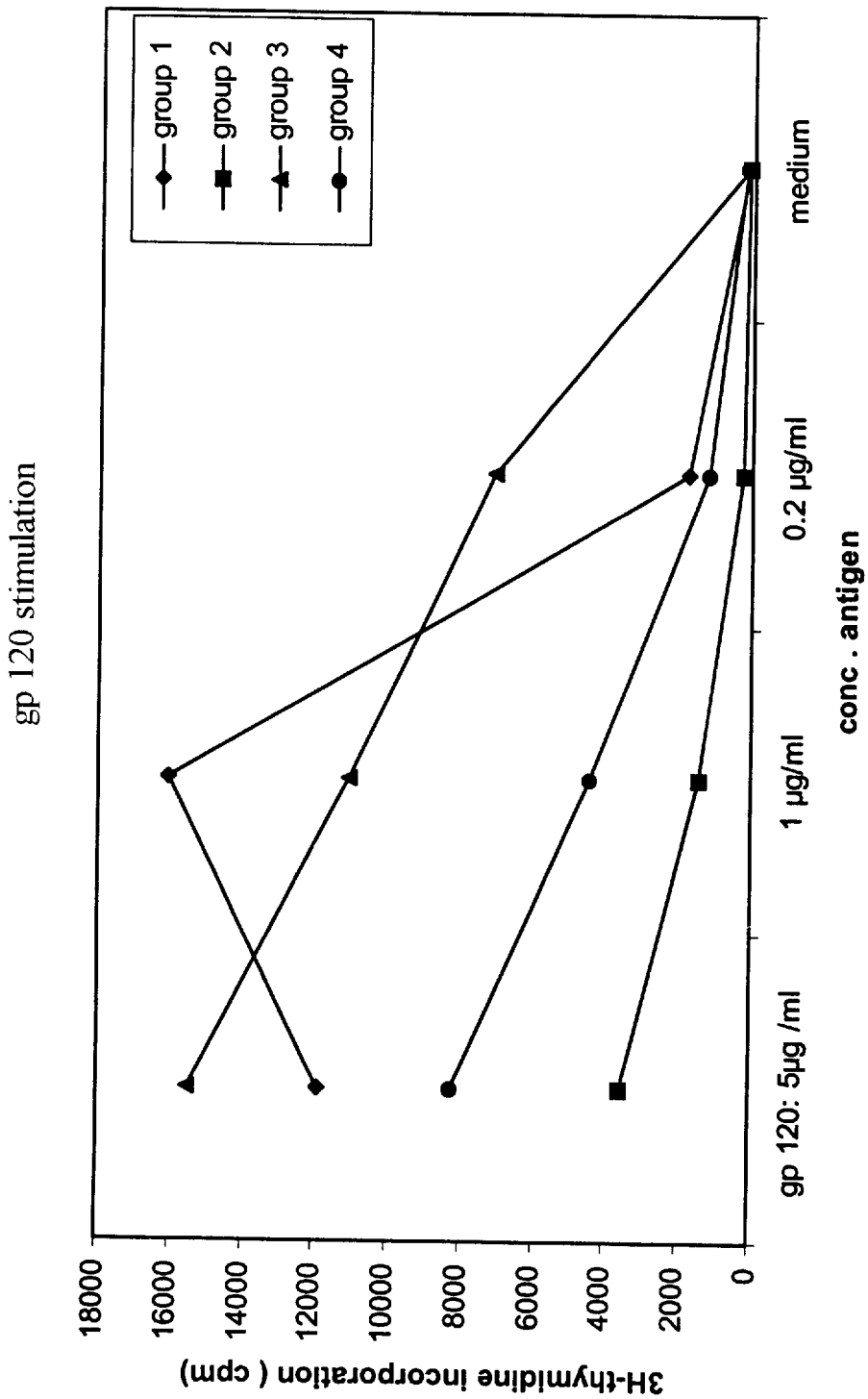

Analysis of lymphoproliferation responses did not show any significant differences is in reactivity to RTS,S between the groups. In contrast, the groups 1 and 3 containing both. CpG and DQS21, showed better gp120-specific Lymphoprolypheration responses than the groups containing CpG or DQS21 alone (FIG. 6).

Figure 7:
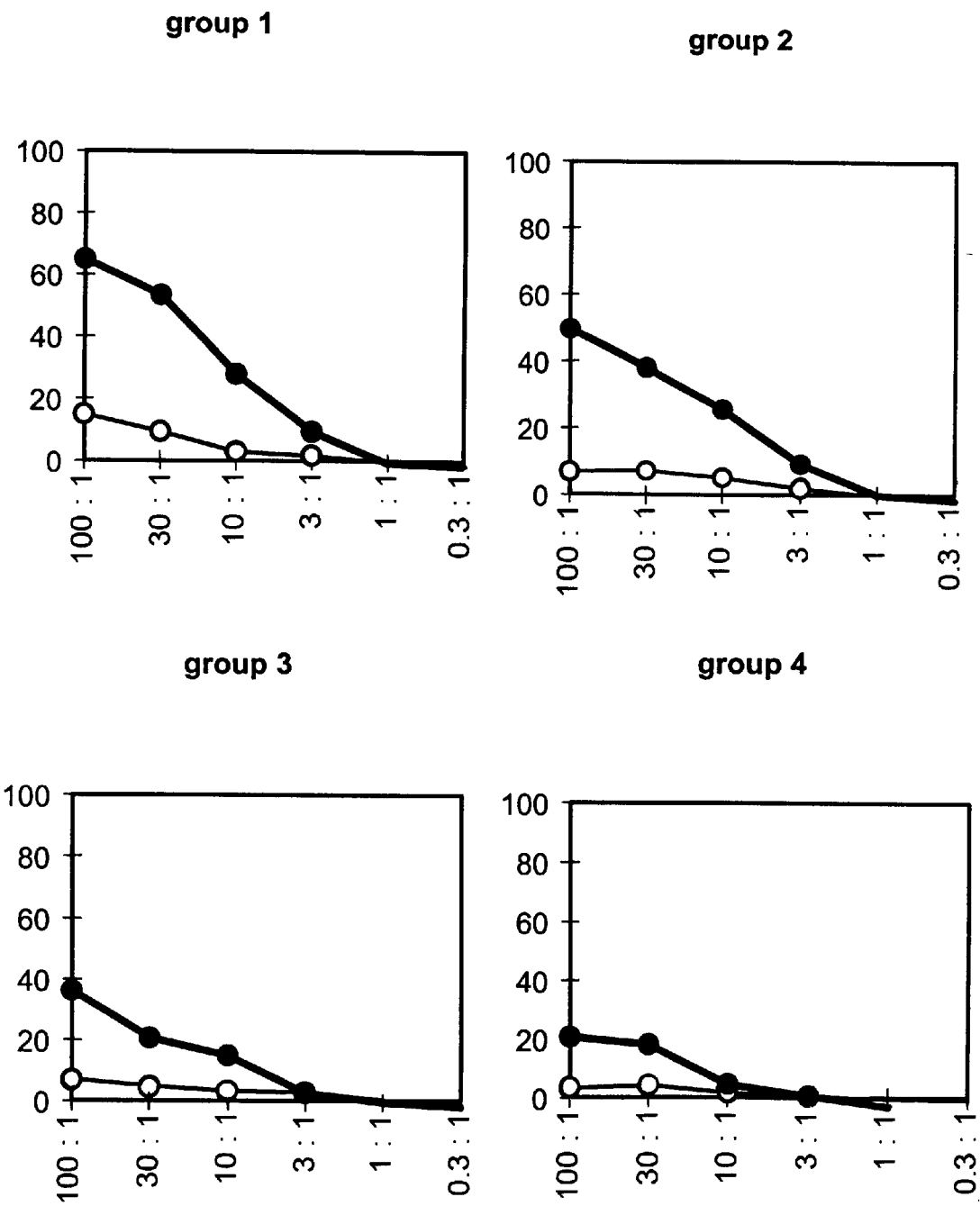

In this experiment only HBsAg-specific CTL were measured. There was no pronounced difference in CTL induction between the groups 1 and 3 having received CpG and DQS21 in combination and the groups 2 and 4 immunized with only one of the two adjuvant components, while the presence of Al(OH)$_3$ diminished the CTL activity observed for the combination of CpG and DQS21 in group 1(FIG. 7). However, a trend was present that CpG and DQS21 was better than DQS21 alone, and the combination induced more CTL in the presence of Al(OH)$_3$ than CpG alone (FIG. 7).

Figure 8:
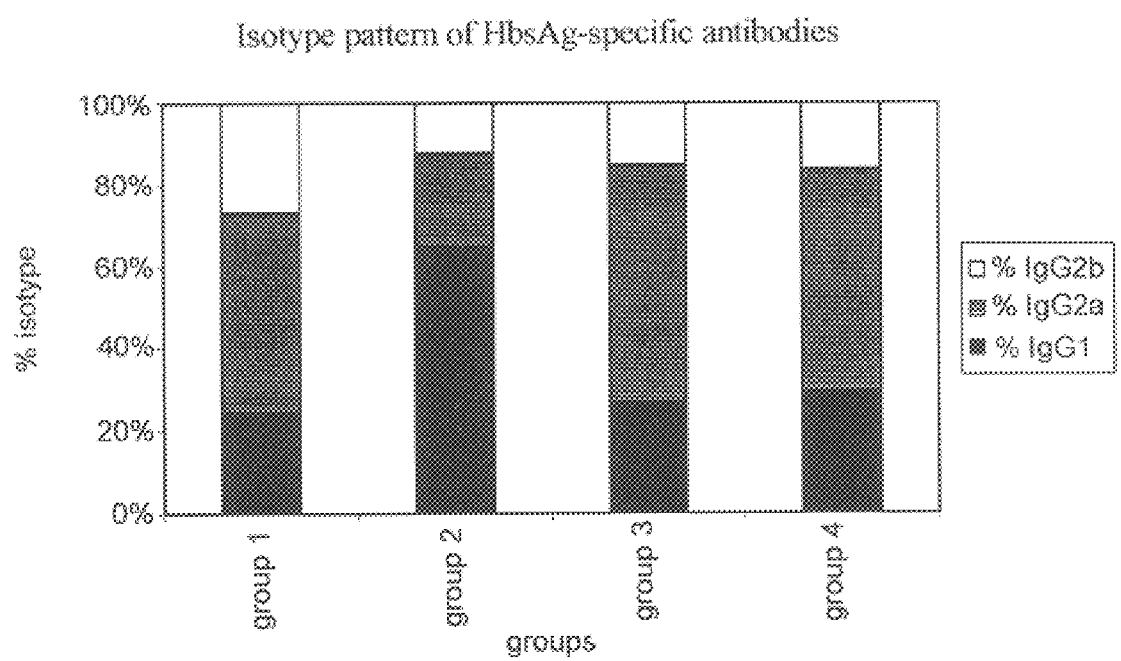

The humoral immune response of the mice was examined only for the presence of HBsAg-specific antibodies. Titers were similar in all groups expect for group 3, which showed an approximately three-fold increase, demonstrating that, in the presence of Al(OH)$_3$, the combination of DQS21 and CpG is more immunogenic than CpG alone (FIG. 8). The isotype distribution was similar for the Al(OH)$_3$-containing groups 3 and 4, while in the absence of Al(OH)$_3$ the combination of CpG and DQS21 induced a stronger $T_{H1}$-like isotype pattern than DQS21 alone (FIG. 8).

Experiment 2

Figure 9A:
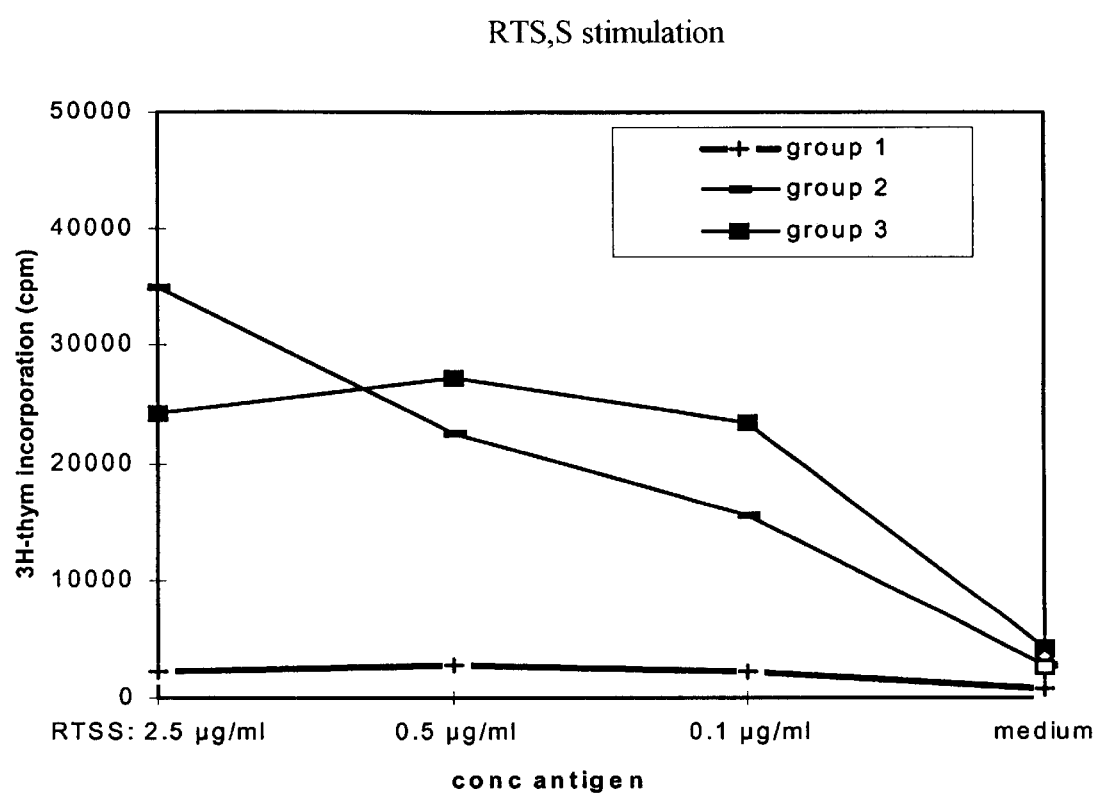
Figure 9B:
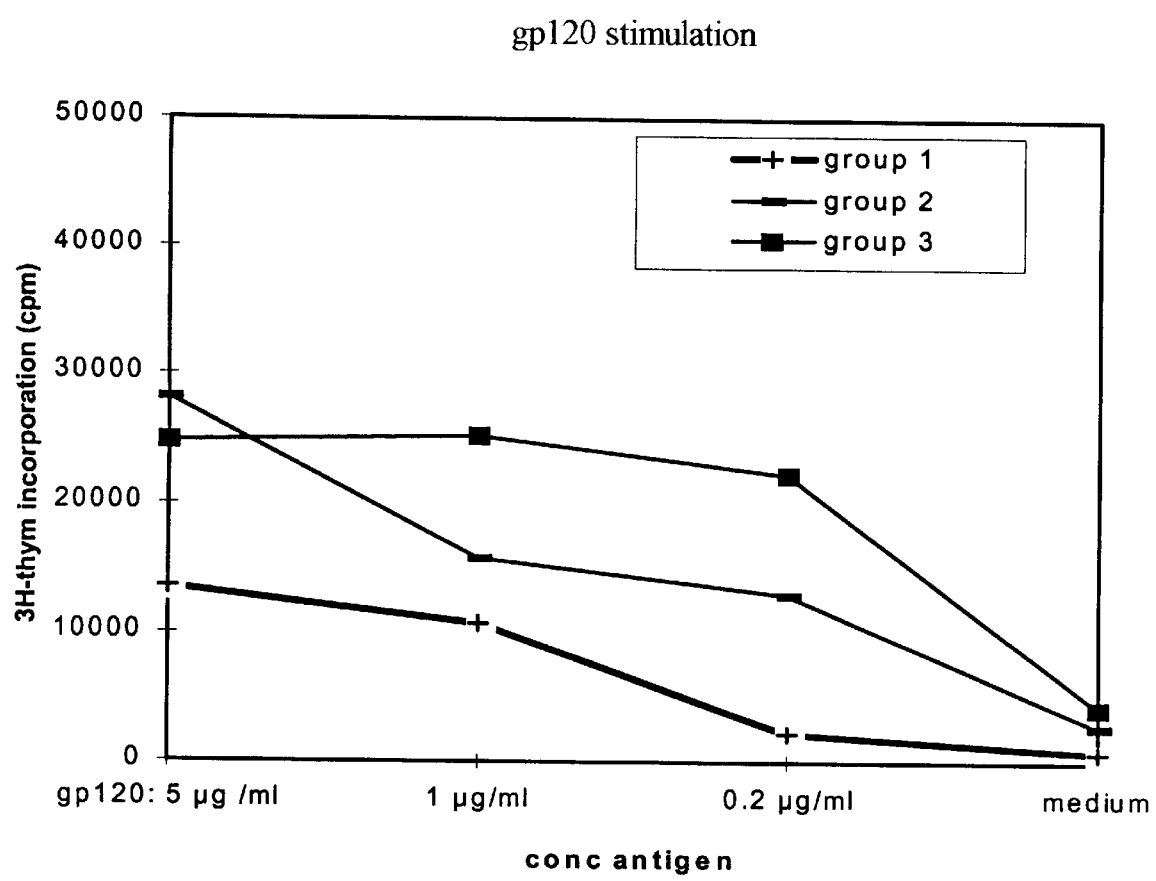

Lymphoproliferation responses specific for RTS,S and gp120 were very similar in this experiment. The data indicate that the addition of DQS21 (either alone or with an o/w emulsion) enhances lymphoproliferation responses to both antigens (FIG. 9).

CTL responses were evaluated by using both, an HBsAg and a gp120 CTL epitope peptide. In both cases, CTL could be detected after immunization of group 1 with CpG alone (FIG. 10). However, addition of DQS21 resulted in a considerable increase in CTL for both antigens (FIG. 10). The presence of an o/w emulsion either neutralized the positive effect of DQS21 (gp120) or increased the background of the in Vitro assay (HBsAg).

Figures 11A, 11B:
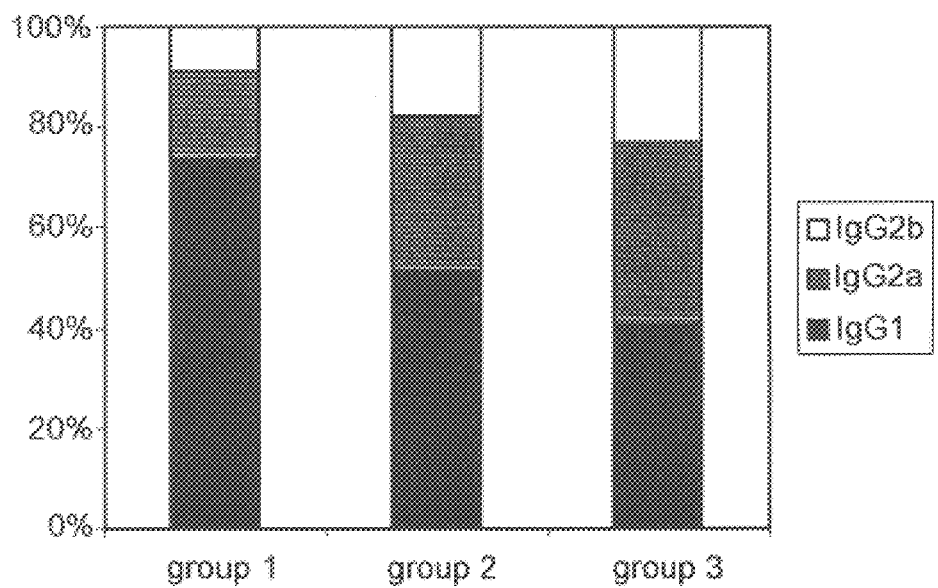

Antibody responses to HBsAg and gp120 increased by addition of DQS21 to the CpG adjuvant (FIG. 11A). A further increase was observed when an o/w emulsion was included in the formulation (FIG. 11A). Addition of DQS21 to CpG shifted the gp120 isotype profiles towards a more pronounced $T_{H1}$ bias (FIG. 11B), while the impact on the HBsAg isotype profiles was less pronounced in this experiment.

5. Conclusions

Immunization with RTS,S and gp120 formulated with the combination of CpG and DQS21 results in strong antigen-specific immune responses. The combination of the adjuvant components CpG and DQS21.

enhances lymphoproliferation responses increases CTL activity augments antibody titers and $T_{H1}$ isotype patterns as compared to the single components.

EXAMPLE 5

Therapeutic Potential of CpG and/or DQS21 Formulations in TC1 Tumour Model

1. Experimental Design

Four groups of 10 mice C57bl/6 received 10e6 (200 µl) TC1 cells (E7 expressing tumour cell) subcutaneous at day 0 in the flank. Mice were then vaccinated twice at day 14 and 21 after the tumour challenge, with 5 µg of formulated PD1/3E7 HPV16 injected intra-footpad. Tumour growth was measured individually twice a week. Groups of mice:

1. No vaccine
2. PD1/3E7+CPG (10 µg ODN 2006)
3. PD1/3E7+DQS21 (0.5 µg)
4. PD1/3E7+CPG+DQS21

The tumour growth was monitored by measuring individual tumours, twice a week.

2. Formulations

Formulations were performed the days of injections. The volume of injection for one mouse was 100 µl. When needed, PD1/3E7 (5 µg) was diluted with H$_2$O and PBS pH 7.4 for isotonicity. After 5 min., if needed QS21 (0.5 µg) mixed with liposomes in a weight ratio QS21/cholesterol of 1/5 (referred to as DQ) was added to the formulation. 30 min later, for the formulation with the oligo, 10 µg of CpG (ODN 2006) was added 30 min prior addition of 1 µg/ml of thiomersal as preservative.

Figure 12:
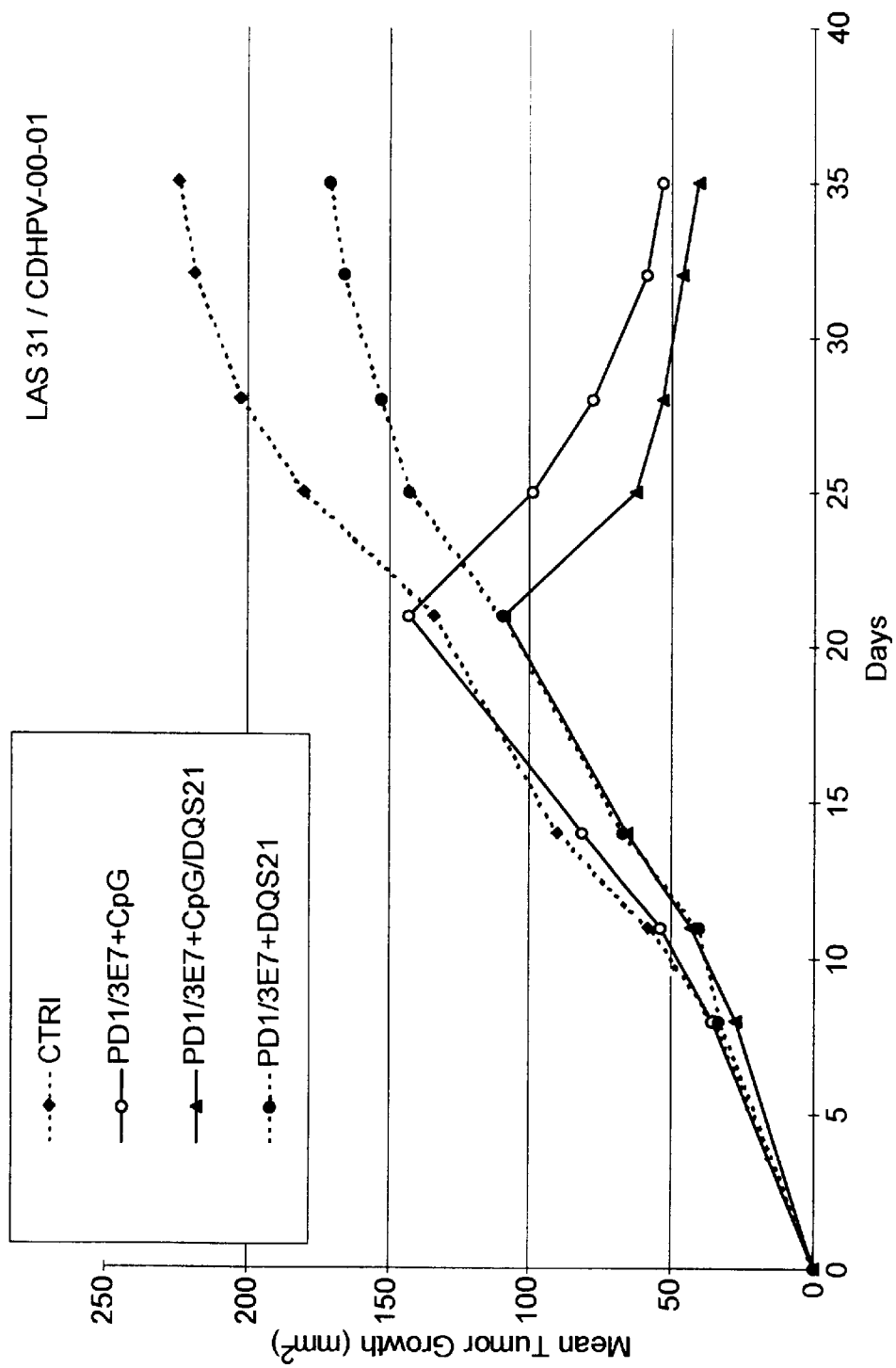

H$_2$O + PBS pH 7.4 + PD1/3E7 - $_{5\ min}$ + DQ - $_{30\ min}$ + CpG - $_{30\ min}$ - Thio 3. Results The evolution of the mean tumour growth per groups of 10 animals over time is shown in FIG. 12. 100% of the animals tat received a tumour challenge of 10e6 TC1 cells progressively developed growing tumour. 70–80% of the non vaccinated animals or of the animals vaccinated with the E7 protein in DQS21 died by day 35. Two vaccinations with the F7 protein formulated in DQS21 had almost no effect on tumour growth. On the contrary, 2 vaccinations, IFP (day 14, 21) with 5 µg ProtD ⅓ E7 HPV16 in CPG adjuvant induced the regression of these pre-established tumours and protect mice from dying 70–80% of the mice were still alive at day 35.

The combination of the 2 immunostimulants CPG and DQS21 showed a slight beneficial effect over the CpG used alone.

EXAMPLE 6

ECD-PD was produced in CHO cells according to the methods of WO 00/44899. The formulations were tested in mice and rabbits.

Formulations were compared against a number of controls.

SBAS+SBAS7

ECD-PD formulated with CpG oligonucleotide 2006 3D-MPL, QS21 in an oil in water emulsion in lipsomes.

SBAS1 Formulation

Comprising QS21 in liposomes and 3D-MPL associated with the lipsomes were prepared according to the procedures of EP 0822831.

SBAS1+SBAS7 Formulation

To the formulation above CpG oligonucleotide 2006 was added. The antigen was admixed to the adjuvant formulation prior to use.

SBAS7+SBAS2-based Formulations (Mice)

For one dose of 50 μl of vaccine, the ECD-PD protein (25 μg) was diluted in 10 fold concentrated PBS pH 6.8 and H2O before consecutive addition of an oil in water emulsion comprising SB62: which is prepared by and comprises 5% squalene 5% tocopherol 2.0% tween 80; the particle size was 180 nm.

Preparation of Emulsion SB62 (2 Fold Concentrate)

Tween 80 is dissolved in phosphate buffered saline (PBS) to give a 2% solution in the PBS. To provide 100 ml two fold concentrate emulsion 5 g of DL alpha tocopherol and 5 ml of squalene are vortexed to mix thoroughly. 90 ml of PBS/Tween solution is added and mixed thoroughly. The resulting emulsion is then passed through a syringe and finally microfluidised by using an M11OS microfluidics machine. The resulting oil droplets have a size of approximately 180 nm., 3D-MPL (10 μg), QS21 (10 μg). 50 μg CpG ODN 2006 were then added followed, 30 minute later by the addition of 50 μg/ml thiomersal as preservative. All incubations were carried out at room temperature with agitation.

SBAS 2 formulations were prepared as above, but without the addition of the CpG oligonucleotide.

BAS7 is CpG Oligonucleotide 2006

BAS7+SBAS2-based Formulations (Rabbit)

For one dose of 500 μl of vaccine, the ECD-PD protein (100 μg) was diluted in 10 fold concentrated PBS pH 6.8 and H2O before consecutive addition of SB62 250 μl, 3D-MPL (100 μg), QS21 (100 μg) and 500 μg of CpG ODN 2006 followed 30 minute later, by the addition of 50 μg/ml thiomersal as preservative. All incubations were carried out at room temperature with agitation.

Tumour Challenge Experiments

Groups of F1 (C57×Balb c) mice (8 mice/group) were injected with 1/10 of the human dose of ECD-PD antigen (25 μg) at days 0–14–2842 and challenged at day 56 with TC1 cells transduced with Her2/neu. The challenge does was administered (2 10e6 TC1 Her2cell) subcutaneously.

As shown in the FIG. 13 the addition of a CpG oligonucleotide to a 3D-MPL/QS21 formulation synergistically enhances tumour regression.

Immunogenicity of ECD-PD in Different Adjuvants in Rabbits 6 groups of 4 rabbits were immunised at days 0, 21 and 42 respectively with 100 μg of ECD-PD in AS02, AS01, AS05, AS06 (CpG 2006 absorbed on alum), AS07 and AS02+AS07.

Serology was analysed 14 days post III and is graphically depicted in FIG. 14.

|  | pre | 14postIII |
| --- | --- | --- |
| AS02B | 50 | 96923 |
| AS01B | 173 | 196637 |
| AS5 | 144 | 76221 |
| AS6 | 142 | 74180 |
| AS07A | 480 | 3904 |
| AS02B + AS07A | 94 | 362713 |

Conclusion

Post 3 injections, the antibody induction is

AS02B+AS07A>AS01B>AS02B=AS06=AS05>AS07A

GENERAL CONCLUSION

The adjuvant tested (AS1, AS2, AS7) have similar effect. However, the combination of AS1 and AS7 or AS2 and AS7 are more effective.

CMI is clearly shown after 4 vaccinations in these animals on the whole molecule ECD-PD but also on each part separately (ECD and ICD).

The formulations of the present invention are very effective in inducing tumour regression.

What is claimed is:

1. An adjuvant composition comprising a QS21 and an immunostimulatory oligonucleotide containing an unmethylated CG dinucleotide.

2. An adjuvant composition according to claim 1 further comprising a carrier.

3. An adjuvant composition as claimed in claim 1, wherein said immunostimulatory oligonucleotide comprises a Purine, Purine, C, G, pyrimidine, pyrimidine sequence.

4. An adjuvant composition as claimed in claim 1, wherein said immunostimulatory oligonucleotide is selected from the group comprising: TCC ATG ACG TTC CTG ACG TT (SEQ ID NO:1); TCT CCC AGC GTG CGC CAT (SEQ ID NO:2); ACC GAT GAC GTC GCC GGT GAC GGC ACC ACG (SEQ ID NO:3); TCG TCG TTT TGT CGT TTT GTC GTT (SEQ ID NO:4); TCC ATG ACG TTC CTG ATG CT (SEQ ID NO:5).

5. An adjuvant composition as claimed in claim 1, wherein the immunostimulatory oligonucleotide contains at least two unmethylated CG repeats being separated at least by 3 nucleotides.

6. An adjuvant composition according to claim 5, wherein the immunostimulatory oligonucleotide contains at least two unmethylated CG repeats being separated by 6 nucleotides.

7. An adjuvant composition as claimed in claim 2, wherein said carrier is a particulate carrier selected from the group comprising metallic salt particles, emulsions, polymers, liposomes, ISCOMs.

8. An immunogenic composition comprising an adjuvant composition as claimed in claims 1 or 2, further comprising an antigen.

9. An immunogenic composition as claimed in claim 8, wherein said antigen is derived from an organism selected from the group comprising: Human Immunodeficiency Virus, Varicella Zoster virus, Herpes Simplex Virus type 1, Herpes Simplex virus type 2, Human cytomegalovirus, Dengue virus, Hepatitis A, B, C or E, Respiratory Syncytial virus, human papilloma virus, Influenza virus, Hib, Meningitis virus, Salmonella, Neisseria, Borrelia, Chlamydia, Bordetella, Streptococcus, Mycoplasma, Mycobacteria, Haemophilus, Plasmodium or Toxoplasma, stanworth decapeptide; or the N terminal 39–43 amino acid fragment (Abeta) of the amyloid precursor protein or antigens associated with atheroschlerosis.

10. An immunogenic composition as claimed in claim 8 wherein the vaccine is administered systemically.

11. An immunogenic composition as claimed in claim 8 wherein the vaccine is administered mucosally.

12. A delivery device pre-filled with the immunogenic composition of claim 8, said device being designed to administer the immunogenic composition systemically.

13. An adjuvant composition according to claim 1 or 2, wherein QS21 is in the form of a liposome.

14. An adjuvant composition according to claim 1 or 2, wherein QS21 is in the form of an oil in water emulsion.

15. An adjuvant composition as claimed in claim 7, wherein the metallic salt particle is aluminium hydroxide or aluminium phosphate.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Human

<400> SEQUENCE: 1
tccatgacgt tcctgacgtt                                            20

<210> SEQ ID NO 2
<211> LENGTH: 18
<212> TYPE: DNA
<213> ORGANISM: Human

<400> SEQUENCE: 2
tctcccagcg tgcgccat                                              18

-continued

```
<210> SEQ ID NO 3
<211> LENGTH: 30
<212> TYPE: DNA
<213> ORGANISM: Human

<400> SEQUENCE: 3
accgatgacg tcgccggtga cggcaccacg                                    30

<210> SEQ ID NO 4
<211> LENGTH: 24
<212> TYPE: DNA
<213> ORGANISM: Human

<400> SEQUENCE: 4
tcgtcgtttt gtcgttttgt cgtt                                          24

<210> SEQ ID NO 5
<211> LENGTH: 20
<212> TYPE: DNA
<213> ORGANISM: Human

<400> SEQUENCE: 5
tccatgacgt tcctgatgct                                               20
```